(12) United States Patent
Fang et al.

(10) Patent No.: US 7,723,393 B2
(45) Date of Patent: May 25, 2010

(54) CYCLOALKYLIDENE COMPOUNDS AS SELECTIVE ESTROGEN RECEPTOR MODULATORS

(75) Inventors: Jing Fang, Durham, NC (US); Dennis Heyer, Durham, NC (US); Subba Reddy Katamreddy, Durham, NC (US); Kenneth William Batchelor, Durham, NC (US); Richard Dana Caldwell, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 147 days.

(21) Appl. No.: 11/915,436

(22) PCT Filed: May 24, 2006

(86) PCT No.: PCT/US2006/020185

§ 371 (c)(1),
(2), (4) Date: Nov. 26, 2007

(87) PCT Pub. No.: WO2006/127871

PCT Pub. Date: Nov. 30, 2006

(65) Prior Publication Data

US 2008/0167360 A1    Jul. 10, 2008

Related U.S. Application Data

(60) Provisional application No. 60/684,433, filed on May 25, 2005.

(51) Int. Cl.
*A01N 35/00* (2006.01)
*C07D 309/00* (2006.01)

(52) U.S. Cl. ........................ 514/683; 514/754; 514/766; 562/468; 549/356

(58) Field of Classification Search .................. 562/468; 514/256, 317, 336, 381, 406, 568, 683, 754, 514/766; 549/356

See application file for complete search history.

(56) References Cited

FOREIGN PATENT DOCUMENTS

| JP | 2000 072612 A | 3/2000 |
| WO | 2005/012220 A2 | 2/2005 |

OTHER PUBLICATIONS

Muthyala R.S.; Bridged Bicyclic Cores Containing A 1,1-Diarylethylene Motif Are High-Affinity Subtype-Selective Ligands For The Estrogen Receptor; Journal of Medicinal Chemistry; 2003; vol. 46, No. 9; 1589-1602; American Chemical Society, US.

*Primary Examiner*—Porfirio Nazario-Gonzalez
*Assistant Examiner*—Yate' K Cutliff
(74) *Attorney, Agent, or Firm*—J. Scott Young

(57) ABSTRACT

The present invention relates to compounds of formula (I) with a variety of therapeutic uses, more particularly the substituted cyclic alkylidene compounds are useful for selective estrogen receptor modulation.

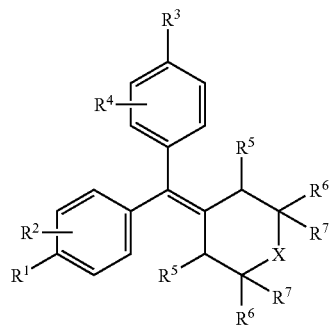

(I)

7 Claims, No Drawings

CYCLOALKYLIDENE COMPOUNDS AS SELECTIVE ESTROGEN RECEPTOR MODULATORS

CROSS-REFERENCE TO RELATED APPLICATIONS

This application is filed pursuant to 35 USC 371 as a United States National Phase Application of International Patent Application Serial No. PCT/US2006/020185 filed on May 24, 2006, which claims priority from 60/684,433 filed on May 25, 2005 in the United States.

FIELD OF THE INVENTION

The present invention relates to novel compounds with a variety of therapeutic uses, more particularly novel substituted cycloalkylidene compounds that are particularly useful for selective estrogen receptor modulation.

BACKGROUND OF THE INVENTION

Estrogens are well-known endocrine regulators in the cellular processes involved in the development and maintenance of the reproductive system. Estrogens have also been shown to have important effects in many non-reproductive tissues such as bone, liver, the cardiovascular system, and the central nervous system. The most widely accepted hypothesis of how estrogens exert their effects is by binding to an intracellular steroid hormone receptor. After the receptor and bound ligand are transferred to the nucleus of the cell, the complex binds to recognition sites in DNA, which allows for the modulation of certain genes. Additionally, it is now becoming apparent that estrogens may mediate their effects via membrane-initiated signaling cascade, though much of this work is still experimental. Kousteni et al., *Journal of Clinical Investigation*, (2003), 111, 1651-1664, herein incorporated by reference with regard to such teaching.

Certain substances have demonstrated the ability to exhibit their biological activity in a "tissue-selective" manner. In other words, tissue selectivity allows functionality as estrogen agonists in certain tissues, while acting as estrogen antagonists in other tissues. The term "selective estrogen receptor modulators" (SERMs) has been given to these molecules. Examples of SERMs include tamoxifen, raloxifene, lasofoxifene, clomiphene, and nafoxidine. The molecular basis for this tissue-selective activity is not completely understood. Without being limited to any particular theory, the ability of the ligand to place the estrogen receptor into different conformational states and allowing for differential capabilities in recruiting coactivator and corepressor proteins, as well as other important proteins involved in transcriptional regulation, is believed to play a role. See, McDonnell, D. P., *The Molecular Pharmacology of SERMs*, Trends Endocrinol. Metab. 1999, 301-311, herein incorporated by reference with regard to such description.

Historically estrogens were believed to manifest their biological activity through a single estrogen receptor, now termed estrogen receptor alpha (ERα). More recently, however, there was the discovery of second subtype of estrogen receptor, termed estrogen receptor beta (ERβ). See, Kuiper et al., WO 97/09348 and Kuiper et al., *Cloning of a Novel Estrogen Receptor Expressed in Rat Prostate and Ovary*, Proc. Natl. Acad. Sci. U.S.A., 1996, pp. 5925-5930, herein incorporated by reference with regard to such subtype. ERβ is expressed in humans. See, Mosselman et al., *ERβ: Identification and Characterization of a Novel Human Estrogen Receptor*, FEBR S Lett., 1996, pp. 49-53, herein incorporated by reference with regard to such expression. The discovery of this second subtype of estrogen receptor significantly increased the biological complexity of estrogen signaling and may be responsible for some of the tissue-selective actions of the currently available SERMs.

As noted above, estrogens have important effects in many non-reproductive tissues. Thus, estrogen modulation is believed useful in the treatment or prophylaxis of diseases and conditions associated with such tissues, including bone, liver, and the central nervous system. For example, osteoporosis is characterized by the net loss of bone mass per unit volume. Such bone loss results in a failure of the skeleton to provide adequate structural support for the body, thereby creating an increased risk of fracture. One of the most common types of osteoporosis is postmenopausal osteoporosis, which is associated with accelerated bone loss subsequent to cessation of menses and declining levels of endogenous estrogen in women. There is an inverse relationship between densitometric measures of bone mass and fracture risk, for peri- and postmenopausal women in the process of rapid bone loss due to declining levels of estrogen. See, Slemenda, et al., *Predictors of Bone Mass in Perimenopausal Women, A Prospective Study of Clinical Data Using Photon Abrsorptiometry*, Ann. Intern. Med., 1990, pp. 96-101 and Marshall, et al., *Meta-Analysis of How Well Measures of Bone Mineral Density Predict Occurrence of Osteoporotic Fractures*, Br Med. J., 1996, pp. 1254-1259, each of which is herein incorporated by reference with regard to such relationship. Elderly women currently have a lifetime risk of fractures of about 75%. In addition there is an approximate 40% risk of hip fracture for Caucasian women over age 50 in the United States. The economic burden from osteoporotic fractures is considerable because of the necessity of hospitalization. In addition, although osteoporosis is generally not thought of as life-threatening, the mortality within 4 months of hip fracture is currently approximately 20 to 30%. Current therapies for postmenopausal osteoporosis include hormone replacement therapy or treatment with other antiresorptive agents such as bisphosphonates or calcitonin. Similarly, SERMS have been shown to be effective in the treatment of postmenopausal osteoporosis (see, Lindsay, R.: *Sex steroids in the pathogenesis and prevention of osteoporosis*. In: Osteoporosis 1988. Etiology, Diagnosis and Management. Riggs B L (ed)l, Raven Press, New York, USA (1988):333-358; Barzel U S: *Estrogens in the prevention and treatment of postmenopausal osteoporosis: a review. Am J. Med* (1988) 85:847-850; and Ettinger, B., Black, D. M., et al., *Reduction of Vertebral Fracture Risk in Postmenopausal Women with Osteoporosis Treated with Raloxifene, JAMA,* 1999, 282, 637-645, each of which is incorporated by reference with regard to such teaching).

As another example, the effects of estrogens on breast tissue, particularly breast cancer, have been well documented. For example, a previously identified SERM, tamoxifen, decreases the risk of recurrent breast cancer, contralateral breast cancer, and mortality as well as increases the disease-free survival rate of patients with breast cancer at multiple stages of the disease. See, Cosman, F., Lindsay, R. *Selective Estrogen Receptor Modulators: Clinical Spectrum*, Endocrine Rev., 1999, pp. 418-434, herein incorporated by reference with regard to such teaching. The profile of tamoxifen, however, is not ideal due to potential interactive properties on reproductive tissues, such as uterine tissues. There is room for an improved therapy for the treatment of such cancers, namely a SERM with no agonist properties on any reproductive tissues.

Cardiovascular disease is the leading cause of death among postmenopausal women. Until recently, the preponderance of data suggested that estrogen replacement therapy in postmenopausal women reduced the risk of cardiovascular disease, although some studies reported no beneficial effect on overall mortality. See, Barrett-Connor, E. et al., *The Potential of SERMs for Reducing the Risk of Coronary Heart Disease*, Trends Endocrinol. Metab., 1999, pp. 320-325, herein incorporated by reference. The mechanism(s) by which estrogens were believed to exert their beneficial effects on the cardiovascular system are not entirely clear. Potentially estrogen's effects on serum cholesterol and lipoproteins, antioxidant properties, vascular smooth muscle proliferation, and inhibition of arterial cholesterol accumulation were believed to play a role. Id. See also, Cosman, F., Lindsay, R. *Selective Estrogen Receptor Modulators: Clinical Spectrum*, Endocrine Rev., 1999, pp. 418-434, herein incorporated by reference. In light of the recent reports of the HERS II and WHI studies, however, continuous combined Hormone Therapy, namely, CEE+MPA [Conjugated Equine Estrogen+Medroxy Progesterone Acetate], confers no cardiovascular benefit in menopausal women. See, Hulley S., Grady, D., Bush, T., et al., *Randomized trial of estrogen plus progestin for secondary prevention of coronary heart disease in postmenopausal women*. Heart and Estrogen/progestin Replacement Study (HERS) Research Group. *J. Am. Med. Assoc.* (1998) 280:605-613 and Wassertheil-Smoller S., Hendrix, S. L., Limacher, M., et al., for the WHI Investigators. *Effect of estrogen plus progestin on stroke in postmenopausal women: the Women's Health Initiative: a randomized trial. JAMA* (2003) 289, 2673-2684, each herein incorporated by reference with regard to such teaching). To what extent these findings may be extrapolated to SERMs is an issue that remains to be determined.

Other therapeutic alternatives include estrogen replacement therapy and/or hormone replacement therapy, which may be useful in the treatment of vasomotor symptoms, genitourinary atrophy, depression, and diabetes. Over 75% of women experience vasomotor symptoms during the climacteric years. Clinical signs, such as vasomotor symptoms and genitourinary atrophy, abate upon treatment with estrogen replacement therapy. Sagraves, R., *J. Clin. Pharmacol.* (1995), 35 (9 Suppl):2S-10S, herein incorporated by reference with regard to such teaching. Preliminary data suggest that estradiol may alleviate depression during perimenopause and that the combination of estrogens and selective serotonin reuptake inhibitors may alleviate depression during the postmenopausal period. Soares, C. N., Poitras, J. R., and Prouty, J., *Drugs Aging*, (2003), 20(2), 85-100, herein incorporated by reference with regard to such teaching. Furthermore, hormone replacement therapy may improve glycemic control among women with diabetes. Palin, S. L. et al., *Diabetes Research and Clinical Practice*, (2001), 54, 67-77; Ferrara, A. et al., *Diabetes Care*, (2001), 24(7), 1144-1150), each incorporated herein by reference with regard to such teaching. There is a need, however, for improved therapies that present better side effect profiles.

The present inventors discovered a novel group of cycloalkylidene compounds, which bind to and modulate estrogen receptor alpha and estrogen receptor beta. As SERMS, these compounds are believed to be useful for the treatment and/or prophylaxis of menopausal or postmenopausal disorders, vasomotor symptoms, urogenital or vulvar vaginal atrophy, atrophic vaginitis, female sexual dysfunction, breast cancer, depressive symptoms, diabetes, bone demineralization, and the treatment and/or prevention of osteoporosis.

SUMMARY OF THE INVENTION

The present invention includes one or more compound(s) of formula (I):

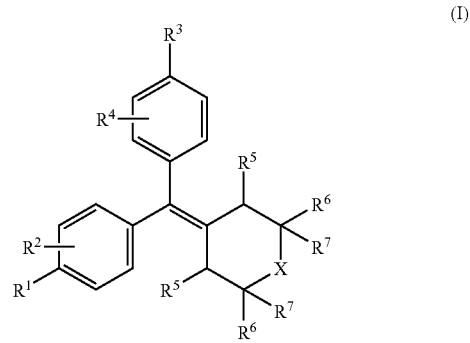

including salts, solvates, and pharmacologically functional derivatives thereof, wherein $R^1$ is H or F;

$R^2$ and $R^4$ each independently are selected from H, OH, alkyl, alkenyl, alkynyl, alkoxy, halogen, haloalkyl, or cyano;

$R^3$ is —$(Y)_z$—$R^8$;

z is 0 or 1;

Y is —C≡C— or —$CR^e$=$CR^f$—;

each $R^5$ is H; or both $R^5$s together combine to form a bridging alkylene chain —$(CH_2)_m$—, where m is 2, 3, or 4, when each $R^6$ and each $R^7$ is H and X is —$(CH_2)_{m-2}$—;

each of $R^6$ and $R^7$ are selected from H or alkyl; or when X is —$(CH_2)_m$—, both $R^6$s are H, and both $R^7$s together combine to form a bridging alkylene chain —$(CH_2)_m$—, where each m is the same and is as defined; or when X is —$(CH_2)_m$—, both $R^7$s are H, and both $R^6$s together combine to form a bridging alkylene chain —$(CH_2)_m$—, where each m is the same and is as defined;

when z is 0, then $R^8$ is alkyl, alkenyl, alkynyl, alkoxy, aryl, heterocyclyl, heterocyclyl substituted with one or more alkyl, cyano, —$O(CH_2)_t CN$, —$CO_2H$, —$(CH_2)_t CO_2H$, —$O(CH_2)_t CO_2H$, —$(CH_2)_t OH$, —$O(CH_2)_t OH$, —$O(CH_2)_t O(CH_2)_t OH$, —$C(O)NR^a R^b$, —$O(CH_2)_t C(O)NR^a R^b$; —$NR^a SO_2 R^d$, or —$NR^a C(O)R^c$;

when z is 1, then $R^8$ is, —$CO_2H$, —$(CH_2)_t CO_2H$, —$(CH_2)_t OH$, —$C(O)NR^a R^b$, or —$PO_3 HR^a$;

each t independently is 1 to 8;

X is —$(CH_2)_n$— where n is 0, 1, 2, or 3, —$C(R^h)_2$—, —O—, —$S(O)_p$ where p is 0, 1, or 2, —$C(R^g)_2 OC(R^g)_2$—, or —$C(CH_2)_v$— where v is 2 to 7 and forms a spirocycle with the depicted ring that contains X;

$R^a$ is H, alkyl, alkenyl, alkynyl, alkoxy, cycloalkyl, aryl, or heterocyclyl;

$R^b$ is H, alkyl, alkenyl, alkynyl, alkoxy, cycloalkyl, aryl, or heterocyclyl;

R$^c$ is alkyl, alkenyl, alkynyl, alkoxy, cycloalkyl, aryl, or heterocyclyl;

R$^d$ is alkyl, alkenyl, alkynyl, alkoxy, cycloalkyl, aryl, or heterocyclyl; or

R$^a$ and R$^b$, R$^a$ and R$^c$, or R$^a$ and R$^d$ may combine with the atoms to which they are bound to form an optionally substituted heterocyclyl; and R$^e$ and R$^f$ each are independently selected from H, alkyl, halogen, and haloalkyl;

R$^g$ is H, alkyl, alkenyl, alkynyl, alkoxy, cycloalkyl, aryl, or heterocyclyl;

R$^h$ is alkyl, alkenyl, alkynyl, alkoxy, cycloalkyl, aryl, or heterocyclyl;

wherein each occurrence of alkyl, alkenyl, alkynyl, cycloalkyl, aryl, and heterocyclyl may be optionally substituted.

More particularly, the present invention includes one or more compound(s) of formula (I-A):

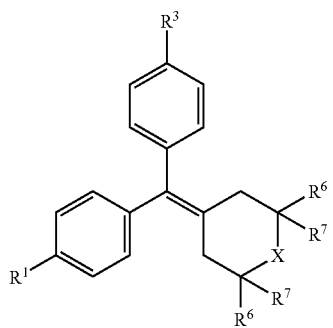

(I-A)

including salts, solvates, and pharmacologically functional derivatives thereof wherein R$^1$ is H or F;

R$^3$ is —(Y)$_z$—R$^8$;

z is 0 or 1;

Y is —CH═CH—;

each of R$^6$ and R$^7$ are selected from H or alkyl;

when z is 0, then R$^8$ is heterocyclyl, heterocyclyl substituted with one or more alkyl, —O(CH$_2$)$_t$CN, —CO$_2$H, —(CH$_2$)$_t$ CO$_2$H, —O(CH$_2$)$_t$CO$_2$H, —O(CH$_2$)$_t$OH, —O(CH$_2$)$_t$O (CH$_2$)$_t$OH, or —O(CH$_2$)$_t$C(O)NH$_2$;

when z is 1, then R$^8$ is —CO$_2$H or —CONH$_2$;

each t independently is 1 to 8; and

X is —(CH$_2$)$_n$—, where n is 0, 1, or 2, or O.

Further, the present invention includes:

(2E)-3-{4-[Cycloheptylidene(phenyl)methyl]phenyl}prop-2-enoic acid;

(2E)-3-{4-[Cycloheptylidene(phenyl)methyl]phenyl}prop-2-enamide;

2-({4-[Phenyl(3,3,5,5-tetramethylcyclohexylidene)methyl]phenyl}oxy)ethanol;

2-{[2-({4-[Phenyl(3,3,5,5-tetramethylcyclohexylidene)methyl]phenyl}oxy)ethyl]oxy}ethanol;

({4-[(4-Fluorophenyl)(3,3,5,5-tetramethylcyclohexylidene)methyl]phenyl}oxy)acetic acid;

4-({4-[(4-Fluorophenyl)(3,3,5,5-tetramethylcyclohexylidene)methyl]phenyl}oxy)butanoic acid;

({4-[(4-Fluorophenyl)(3,3,5,5-tetramethylcyclohexylidene) methyl]phenyl}oxy)acetonitrile;

2-({4-[(4-Fluorophenyl)(3,3,5,5-tetramethylcyclohexylidene)methyl]phenyl}oxy)ethanol;

(2E)-3-{4-[Phenyl(3,3,5,5-tetramethylcyclohexylidene)methyl]phenyl}-2-propenoic acid;

4-[Phenyl(3,3,5,5-tetramethylcyclohexylidene)methyl]benzoic acid;

3,5-Dimethyl-4-{4-[phenyl(3,3,5,5-tetramethylcyclohexylidene)methyl]phenyl}isoxazole;

1-Methyl-4-{4-[phenyl(3,3,5,5-tetramethylcyclohexylidene)methyl]phenyl}1H-pyrazole;

4-{4-[(4-Fluorophenyl)(3,3,5,5-tetramethylyclohexylidene)methyl]phenyl}-3,5-dimethylisoxazole;

3-{4-[(4-Fluorophenyl)(3,3,5,5-tetramethylcyclohexylidene)methyl]phenyl}furan;

2-{[2-({4-[(4-Fluorophenyl)(3,3,5,5-tetramethylcyclohexylidene)methyl]phenyl}oxy)ethyl]oxy}ethanol;

2-{4-[(4-Fluorophenyl)(3,3,5,5-tetramethylcyclohexylidene)methyl]phenyl}furan;

4-{4-[(4-fluorophenyl)(3,3,5,5-tetramethylyclohexylidene) methyl]phenyl}-1-methyl-1H-pyrazole;

4-({4-[Phenyl(3,3,5,5-tetramethylcyclohexylidene)methyl] phenyl}oxy)-1-butanol;

2-({4-[Phenyl(3,3,5,5-tetramethylcyclohexylidene)methyl] phenyl}oxy)acetamide;

({2-Methyl-5-[phenyl(3,3,5,5-tetramethylcyclohexylidene) methyl]phenyl}oxy)acetic acid;

2-({2-Methyl-5-[phenyl(3,3,5,5-tetramethylcyclohexylidene)methyl]phenyl}oxy)ethanol;

({2-Methyl-5-[phenyl(3,3,5,5-tetramethylcyclohexylidene) methyl]phenyl}oxy)acetonitrile;

4-({2-Methyl-5-[phenyl(3,3,5,5-tetramethylcyclohexylidene)methyl]phenyl}oxy)butanoic acid;

4-({2-Methyl-5-[phenyl(3,3,5,5-tetramethylyclohexylidene) methyl]phenyl}oxy)-1-butanol;

5-[({2-Methyl-5-[phenyl(3,3,5,5-tetramethylcyclohexylidene)methyl]phenyl}oxy)methyl]-1H-tetrazole;

2-{[2-({2-Methyl-5-[phenyl(3,3,5,5-tetramethylcyclohexylidene)methyl]phenyl}oxy)ethyl]oxy}ethanol;

4-({4-[Phenyl(3,3,5,5-tetramethylcyclohexylidene)methyl] phenyl}oxy)butanoic acid;

({4-[Phenyl(3,3,5,5-tetramethylcyclohexylidene)methyl] phenyl}oxy)acetic acid;

(2E)-3-{4-[(4-Fluorophenyl)(3,3,5,5-tetramethylcyclohexylidene)methyl]phenyl}-2-propenoic acid;

(2E)-3-{4-[(4-Fluorophenyl)(2,2,6,6-tetramethyltetrahydro-4H-pyran-4-ylidene)methyl]phenyl}-2-propenoic acid;

(2E)-3-{4-[Phenyl(2,2,6,6-tetramethyltetrahydro-4H-pyran-4-ylidene)methyl]phenyl}-2-propenoic acid;

4-{4-[Phenyl(2,2,6,6-tetramethyltetrahydro-4H-pyran-4-ylidene)methyl]phenyl}butanoic acid;

4-{4-[(4-Fluorophenyl)(2,2,6,6-tetramethyltetrahydro-4H-pyran-4-ylidene)methyl]phenyl}butanoic acid;

2-({4-[(4-Fluorophenyl)(2,2,6,6-tetramethyltetrahydro-4H-pyran-4-ylidene)methyl]phenyl}oxy)ethanol;

2-({4-[Phenyl(2,2,6,6-tetramethyltetrahydro-4H-pyran-4-ylidene)methyl]phenyl}oxy)ethanol;

2-{[2-({4-[Phenyl(2,2,6,6-tetramethyltetrahydro-4H-pyran-4-ylidene)methyl]phenyl}oxy)ethyl]oxy}ethanol;

2-{[2-({4-[(4-Fluorophenyl)(2,2,6,6-tetramethyltetrahydro-4H-pyran-4-ylidene)methyl]phenyl}oxy)ethyl] oxy}ethanol;

4-[(4-Fluorophenyl)(2,2,6,6-tetramethyltetrahydro-4H-pyran-4-ylidene)methyl]benzoic acid;

4-[Phenyl(2,2,6,6-tetramethyltetrahydro-4H-pyran-4-ylidene)methyl]benzoic acid; and 4-[(4-Fluorophenyl)(3,3,5,5-tetramethylcyclohexylidene)methyl]benzoic acid, including salts, solvates, and pharmacologically functional derivatives thereof, with reference being had to the examples and illustrated structures herein described.

The present invention further includes a compound

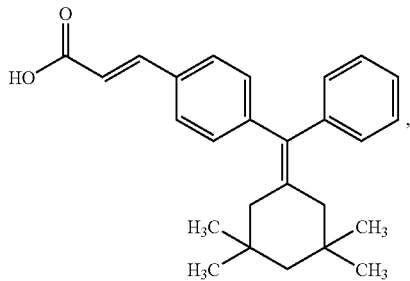

including salts, solvates, and pharmacologically functional derivatives thereof.

The present invention further includes a compound

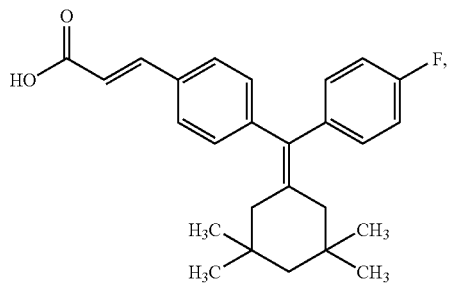

including salts, solvates, and pharmacologically functional derivatives thereof.

The invention includes one or more compound of the present invention substantially as hereinbefore defined with reference to any one of the Examples.

The invention includes a pharmaceutical composition comprising one or more compound of the present invention and a pharmaceutically acceptable carrier.

The invention includes one or more compound of the present invention for use as an active therapeutic substance.

The invention includes one or more compound of the present invention for use in the treatment or prophylaxis of conditions or disorders affected by selective estrogen receptor modulation. Particularly, the invention includes the use of one or more compound of the present invention wherein treatment or prophylaxis relates to osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myaligia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumor cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, systemic lupus erythematosus, amyotrophic lateral sclerosis, stroke, CNS trauma, dementia, neurodegeneration, breast pain and dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), dysmenorrhea, autoimmune diseases, Hashimoto's thyroiditis, SLE (systemic lupus erythematosus), myasthenia gravis, or reperfusion damage of ischemic myocardium. The invention includes the use of one or more compound of the present invention wherein treatment or prophylaxis relates to menopausal or postmenopausal disorders, vasomotor symptoms, urogenital or vulvar vaginal atrophy, atrophic vaginitis, female sexual dysfunction, breast cancer, depressive symptoms, diabetes, bone demineralization, or osteoporosis.

The present invention includes use of one or more compound of the present invention in the manufacture of a medicament for use in the treatment or prophylaxis of conditions or disorders associated with selective estrogen receptor modulation. Further, the invention includes use of one or more compound of the present invention in the manufacture of a medicament for use in the treatment or prophylaxis of osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myaligia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumor cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, systemic lupus erythematosus, amyotrophic lateral sclerosis, stroke, CNS trauma, dementia, neurodegeneration, breast pain and dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), dysmenorrhea, autoimmune diseases, Hashimoto's thyroiditis, SLE (systemic lupus erythematosus), myasthenia gravis, or reperfusion damage of ischemic myocardium. The invention includes use of one or more compound of the present invention wherein the condition or disorder is menopausal or postmenopausal disorders, vasomotor symptoms, urogenital or vulvar vaginal atrophy, atrophic vaginitis, female sexual dysfunction, breast cancer, depressive symptoms, diabetes, bone demineralization, or osteoporosis.

The invention includes a method for the treatment or prophylaxis of conditions or disorders associated with selective estrogen receptor modulation comprising the administration of one or more compound of the present invention. The invention includes a method for the treatment or prophylaxis related to osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myaligia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumor cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, systemic lupus erythematosus, amyotrophic lateral sclerosis, stroke, CNS trauma, dementia, neurodegeneration, breast pain and dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), dysmenorrhea, autoimmune diseases, Hashimoto's thyroiditis, SLE (systemic lupus erythematosus), myasthenia gravis, or reperfusion damage of ischemic myocardium comprising the administration of one or more compound of the present invention. Further, the invention includes one or more compound of the present invention wherein the condition or disorder is menopausal or postmenopausal disorders, vasomotor symptoms, urogenital or vulvar vaginal atrophy, atrophic vaginitis, female sexual dysfunction, breast cancer, depressive symptoms, diabetes, bone demineralization, or osteoporosis.

DETAILED DESCRIPTION OF THE PREFERRED EMBODIMENT

The present invention is described in terms known and appreciated by those skilled in the art. For ease of reference certain terms hereafter are defined. The fact that certain terms are defined, however, should not be considered as indicative that any term that is undefined is indefinite. Rather, all terms used herein are believed to describe the invention in terms such that one of ordinary skill can identify the scope of the present invention.

As used herein the term "alkyl" refers to a straight or branched chain hydrocarbon, for example having from one to twelve carbon atoms. Examples of "alkyl" as used herein include, but are not limited to, methyl, ethyl, propyl, isopropyl, isobutyl, n-butyl, tert-butyl, isopentyl, n-pentyl, and the like.

As used herein the term "alkenyl" refers to a straight or branched chain hydrocarbon that contains one or more carbon-to-carbon double bond, for example having from two to twelve carbon atoms. Examples of "alkenyl" as used herein include, but are not limited to, vinyl, 1-propenyl, allyl, and the like.

As used herein the term "alkynyl" refers to a straight or branched chain hydrocarbon that contains one or more carbon-to-carbon triple bonds, for example having from two to twelve carbon atoms. Examples of "alkynyl" as used herein include, but are not limited to, ethynyl, 1-propynyl, 2-propynyl, and the like.

As used herein, the term "alkylene" refers to a straight or branched chain divalent hydrocarbon radical, for example having from one to ten carbon atoms. Examples of "alkylene" as used herein include, but are not limited to, methylene, ethylene, n-propylene, n-butylene, and the like.

As used herein the term "halogen" refers to fluorine, chlorine, bromine, or iodine.

As used herein the term "haloalkyl" refers to an alkyl group, as defined herein, that is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups and the like.

As used herein the term "alkoxy" refers to the group —OR, where R is alkyl as defined above.

As used herein the term "acyl" refers to the group —C(O)R, where R is alkyl, aryl, or heterocyclyl, as each is defined herein.

As used herein the term "hydroxy" refers to the group —OH.

As used herein the term "carboxy" refers to the group —C(O)OH.

As used herein the term "nitro" refers to the group —$NO_2$.

As used herein the term "amino" refers to the group —$NH_2$, or when referred to as substituted amino defines such groups substituted with alkyl.

As used herein, the term "cycloalkyl" refers to a non-aromatic cyclic hydrocarbon ring, for example having from three to ten carbon atoms. Exemplary "cycloalkyl" groups include, but are not limited to, cyclopropyl, cyclobutyl, cyclopentyl, cyclohexyl, cycloheptyl, and the like.

As used herein, the term "aryl" refers to substituent groups derived from benzene and its derivatives, including fused benzene ring systems, for example, anthracene, phenanthrene, or naphthalene ring systems. Examples of "aryl" groups include, but are not limited to, phenyl, 2-naphthyl, 1-naphthyl, and biphenyl.

As used herein, the term "heterocycle," "heterocyclyl," or "heterocyclic" refers to a mono- or poly-cyclic ring system containing one or more heteroatoms that optionally contains one or more degrees of unsaturation. Preferred heteroatoms include N, O, and/or S, including N-oxides, sulfur oxides, and dioxides. By way of example the heterocyclyl ring system is three to ten-membered and is either saturated or has one or more degrees of unsaturation. Such rings may be optionally fused to one or more of another "heterocyclic" ring(s), aryl ring(s), or cycloalkyl ring(s) and will be referenced as a "heterocycle" group. Examples of "heterocyclic" groups include, but are not limited to, tetrahydrofuran, pyran, 1,4-dioxane, 1,3-dioxane, piperidine, pyrrolidine, morpholine, tetrahydrothiopyran, tetrahydrothiophene, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and the like.

As used herein the term "spirocycle" describes a ring system that includes two rings that share a common atom. Examples of spirocyclic compounds include spiro[4.4] nonane and the like.

The compounds of formulas (I) may crystallize in more than one form, a characteristic known as polymorphism, and such polymorphic forms ("polymorphs") are within the scope of formula (I). Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by formula (I), as well as any wholly or partially equilibrated mixtures thereof. The present invention also includes the individual isomers of the compounds represented by the formulas above as mixtures with isomers thereof in which one or more chiral centers are inverted.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. Representative salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

As used herein, the term "solvate" refers to a complex of variable stoichiometry formed by a solute (in this invention, a compound of Formula I, or a salt or physiologically functional derivative thereof) and a solvent. Such solvents, for the purpose of the invention, should not interfere with the biological activity of the solute. Non-limiting examples of suitable solvents include, but are not limited to, water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of *Burger's Medicinal Chemistry And Drug Discovery*, $5^{th}$ Edition, Vol 1: Principles and Practice, which is incorporated herein by reference to the extent that it teaches physiologically functional derivatives.

As used herein, the term "effective amount" means that amount of a drug or pharmaceutical agent that will elicit the biological or medical response of a tissue, system, animal or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of a compound of formula (I), as well as salts, solvates, and physiological functional derivatives thereof, may be administered as the raw chemical. Additionally, the active ingredient may be presented as a pharmaceutical composition. Accordingly, the invention further provides pharmaceutical compositions that include effective amounts of compounds of the formula (I) and salts, solvates, and physiological functional derivatives thereof, and one or more pharmaceutically acceptable carriers, diluents, or excipients. The compounds of formula (I) and salts, solvates, and physiologically functional derivatives thereof, are as described above. The carrier(s), diluent(s) or excipient(s) must be acceptable, in the sense of being compatible with the other ingredients of the formulation and not deleterious to the recipient of the pharmaceutical composition. In accordance with another aspect of the invention there is also provided a process for the preparation of a pharmaceutical formulation including admixing a compound of the formula (I) or salts, solvates, and physiological functional derivatives thereof, with one or more pharmaceutically acceptable carriers, diluents or excipients.

A therapeutically effective amount of a compound of the present invention will depend upon a number of factors. For example, the age and weight of the animal, the precise condition requiring treatment and its severity, the nature of the formulation, and the route of administration are all factors to be considered. The therapeutically effective amount ultimately should be at the discretion of the attendant physician or veterinarian. For example, an effective amount of a compound of formula (I) for the treatment of humans suffering from osteoporosis, generally, should be in the range of 0.1 to 100 mg/kg body weight of recipient (mammal) per day. More usually the effective amount should be in the range of 1 to 10 mg/kg body weight per day. Thus, for a 70 kg adult mammal the actual amount per day would usually be from 70 to 700 mg. This amount may be given in a single dose per day or in a number (such as two, three, four, five, or more) of sub-doses per day such that the total daily dose is the same. An effective amount of a salt, solvate, or physiologically-functional derivative thereof, may be determined as a proportion of the effective amount of the compound of formula (I) per se. Similar dosages should be appropriate for treatment of the other conditions referred to herein that are mediated by estrogen.

Pharmaceutical formulations may be presented in unit dose forms containing a predetermined amount of active ingredient per unit dose. Such a unit may contain, as a non-limiting example, 0.5 mg to 1 g of a compound of the formula (I), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like. Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders, such as carboxymethylcellulose, aliginates, gelatins, or polyvinyl pyrrolidone, solution retardants, such as paraffin, resorption accelerators such as a quaternary salt and/or abrsorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate dosage unit formulations for oral administration can be microencapsulated. The formulation can also be prepared to prolong or sustain the release as for example by coating or embedding particulate material in polymers, wax or the like.

The compounds of formula (I) and salts, solvates, and physiological functional derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and salts, solvates, and physiologically functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone (PVP), pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3 (6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical formulations adapted for topical administrations to the eye include eye drops wherein the active ingredient is dissolved or suspended in a suitable carrier, especially an aqueous solvent. Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring agents.

The compounds of the present invention and their salts, solvates, and physiologically functional derivatives thereof, may be employed alone or in combination with other therapeutic agents for the treatment of the conditions herein described. For example, in osteoporosis therapy, combination with other osteoporotic agents is envisaged. By way of example, combination therapies according to the present invention thus comprise the administration of at least one compound of formula (I) or a salt, solvate, or physiologically functional derivative thereof or a combination thereof, and the use of at least one other agent. By way of example, in osteoporosis therapy one or more of a compound(s) of the present invention may be combined with a bone building agent.

The amounts of the compound(s) of formula (I) and the other pharmaceutically active agent(s) and the relative timings of administration will be selected in order to achieve the desired combined therapeutic effect. The administration in combination of a compound the present invention with other therapeutic agent(s) may be in combination by administration concomitantly in: (1) a unitary pharmaceutical composition including each compound; or (2) separate pharmaceutical compositions each including one of the compounds. Alternatively, the combination may be administered separately in a sequential manner wherein one treatment agent is administered first and the other(s) subsequently or vice versa. Such sequential administration may be close in time or remote in time. Thus, the combination may be administered together or separately and, when administered separately, administration may occur simultaneously or sequentially in any order.

As noted, one potential additional osteoporosis treatment agent is a bone building (anabolic) agent. Bone building agents can lead to an increase in parameters, such as bone mineral density, that are greater than those than can be achieved with anti-resorptive agents. In some cases, such anabolic agents can increase trabecular connectivity leading to greater structural integrity of the bone.

Other potential therapeutic combinations include the compounds of the present invention combined with growth promoting agents, growth hormone secretagogues, growth hormone releasing factor and its analogs, growth hormone and its analogs, somatomedins, alpha-ardenergic agonists, serotonin 5-$HT_D$ agonists, selective serotonin reuptake inhibitors, agents that inhibit somatostatin or its release, 5-α-reductase inhibitors, aromatase inhibitors, GnRH inhibitors, parathyroid hormone, bisphosphonates, estrogen, testosterone, progesterone receptor agonists, and/or with other modulators of nuclear hormone receptors such as SERMs including other compounds of the present invention.

Non-limiting examples include combinations of one or more compound(s) of the present invention with anti-diabetic agents, anti-osteoporosis agents, anti-obesity agents, anti-inflammatory agents, anti-anxiety agents, anti-depressants, anti-hypertensive agents, anti-platelet agents, anti-thrombotic and thrombolytic agents, cardiac glycosides, cholesterol or lipid lowering agents, mineralocorticoid receptor antagonists, phosphodiesterase inhibitors, kinase inhibitors, thyroid mimetics, anabolic agents, viral therapies, cognitive disorder therapies, sleeping disorder therapies, sexual dysfunction therapies, contraceptives, cytotoxic agents, radiation therapy, anti-proliferative agents, and anti-tumor agents. Additionally, the compounds of the present invention may be combined with nutritional supplements such as amino acids, triglycerides, vitamins, minerals, creatine, piloic acid, carnitine, or coenzyme Q10.

An aspect of the present invention is the use of the compounds of the present invention for the treatment or prophylaxis of a variety of disorders including, but not limited to, osteoporosis, bone demineralization and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumore cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstral syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, amyotrophic lateral sclerosis, stroke, CNS trauma, dementia, neurodegeneration, breast pain, dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), autoimmune diseases, Hashimoto's thyroiditis, SLE (systemic lupus erythematosus), myasthenia gravis, reperfusion damage of ischemic myocardium, In particular, the compounds of the present invention are believed useful, either alone or in combination with other agents, in the treatment of menopausal or postmenopausal disorders, vasomotor symptoms, urogenital or vulvar vaginal atrophy, atrophic vaginitis, female sexual dysfunction, breast cancer, depressive symptoms, diabetes, bone demineralization, and the treatment and/or prevention of osteoporosis.

The compounds of this invention may be made by a variety of methods, including well-known standard synthetic methods. Illustrative general synthetic methods are set out below and then specific compounds of the invention are prepared in the working Examples.

In the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of formula (I).

Those skilled in the art will recognize if a stereocenter exists in compounds of formula (I). Accordingly, the present invention includes all possible stereoisomers and includes not only racemic compounds but the individual enantiomers as well. When a compound is desired as a single enantiomer, such may be obtained by stereospecific synthesis, by resolution of the final product or any convenient intermediate, or by chiral chromatographic methods as are known in the art. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994), incorporated by reference with regard to stereochemistry.

EXPERIMENTAL SECTION

Abbreviations

As used herein the symbols and conventions used in these processes, schemes and examples are consistent with those used in the contemporary scientific literature, for example, the *Journal of the American Chemical Society* or the *Journal of Biological Chemistry*. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
Hz (Hertz); MHz (megahertz);
mol (moles); mmol (millimoles);
RT (room temperature); h (hours);
d (days); EI (electron impact);
min (minutes); TLC (thin layer chromatography);
mp (melting point); RP (reverse phase);
$T_r$ (retention time); TFA (trifluoroacetic acid);
TEA (triethylamine); THF (tetrahydrofuran);
TFAA (trifluoroacetic anhydride); $CD_3OD$ (deuterated methanol);
$CDCl_3$ (deuterated chloroform); DMSO (dimethylsulfoxide);
$SiO_2$ (silica); atm (atmosphere);
EtOAc (EtOAc); $CHCl_3$ (chloroform);
HCl (hydrochloric acid); Ac (acetyl);
DMF (N,N-dimethylformamide); Me (methyl);
$Cs_2CO_3$ (cesium carbonate); EtOH (ethanol);
Et (ethyl); tBu (tert-butyl);
MeOH (methanol); $CH_2Cl_2$ (dichloromethane);
$MgSO_4$ (magnesium sulfate); $CH_3CN$ (acetonitrile);
$K_2CO_3$ (potassium carbonate); $TiCl_4$ (titanium tetrachloride);
EtOAc (EtOAc); $CO_2$ (carbon dioxide);
$Pd(OAc)_2$ (palladium acetate); $Et_2O$ (diethyl ether);
$P(o-tolyl)_3$ (tri-o-tolylphosphine); $Na_2SO_4$ (sodium sulfate);
NaH (sodium hydride); DME (1,2-dimethoxyethane);
NaI (sodium iodide); NaOH (sodium hydroxide);
$NH_4Cl$ (ammonium chloride); $NaHCO_3$ (sodium bicarbonate);
$AlCl_3$ (aluminum chloride); $(C_2H_5O)_2P(O)H$ (diethyl phosphite);
$NaN_3$ (sodium azide); $CBr_4$ (carbon tetrabromide);
$PPh_3$ (triphenylphosphine); CuI (copper (I) iodide);
$Pd(Ph_3P)_4$ (tetrakis(triphenylphosphine)palladium (0));
$(iPrO)_3B$ (triisopropyl borate); nBuLi (butyllithium);
$Na_2CO_3$ (sodium carbonate); DMAP (4-(dimethylamino)pyridine);
eq (equivalents);
HRMS (high resolution mass spectrometry);
LCMS (liquid chromatography mass spectrometry);
LRMS (low resolution mass spectrometry);
APCI (Atmospheric Pressure Chemical Ionization);
LiHMDS (lithium bis(trimethylsilyl)amide);
$Pd(Ph_3P)_2Cl_2$ (dichlorobis(triphenylphosphine)palladium (II));
EDC (N-(3-dimethylaminopropyl)-N'-ethyl-carbodimide;
dpppe (1,5-bis(diphenylphosphanyl)pentane;
DMAc (N,N-dimethylacetamide);
HPLC (high performance liquid chromatography);
tmeda (N,N,N',N'-tetramethylethylenediamine);
$Pd_2(dba)_3$ (dipalladiumtris(dibenzylidene acetone)).

Unless otherwise noted, reagents and solvents were obtained from commercial suppliers and were used without further purification. Unless otherwise indicated, all reactions were conducted at room temperature and all temperatures are expressed in ° C. (degrees Centigrade).

Thin-layer chromatography (TLC) was performed on silica gel 60 $F_{254}$ precoated plates. Detection was effected by exposure to UV light (254 nm). Flash and flush column chromatography was performed using Silica Gel 60. Reverse phase preparative and analytical HPLC were performed using C18 columns and acetonitrile:water gradients with 0.05% TFA as a modifier.

Compound purity and characterization were determined by $^1$H-NMR, liquid chromatography-mass spectrometry (LCMS), high resolution mass spectrometry (HRMS), combustion (elemental) analysis, HPLC, and melting point. Compounds of general formula I were typically found to have purities of >90%.

$^1$H NMR spectra were recorded on Varian INOVA-300 and Varian INOVA-400 instruments. Chemical shifts are expressed in parts per million (ppm, δ units). Coupling constants are in units of hertz (Hz). Splitting patterns describe apparent multiplicities and are designated as s (singlet), d (doublet), dd (doublet of doublet), t (triplet), q (quartet), m (multiplet), or br (broad).

Low resolution mass spectra were obtained on Micromass ZQ, Micromass ZMD, Micromass QuattroMicro, and Micromass GCT instruments from Micromass Ltd., Altricham, UK, using either Atmospheric Pressure Chemical Ionization (APCI) or ESI Ionization (ESI).

High resolution mass spectral data (HRMS) were recorded with Micromass LCT and Micromass GCT instruments.

Combustion analyses were performed by Atlantic Microlab, Inc. (Norcross, Ga.).

Melting points were recorded in open capillary tubes and are uncorrected. The bolded numerals reference the compounds as depicted in the following schemes.

Scheme 1
General Route to Substituted Cycloalkylidene Diphenylethylenes

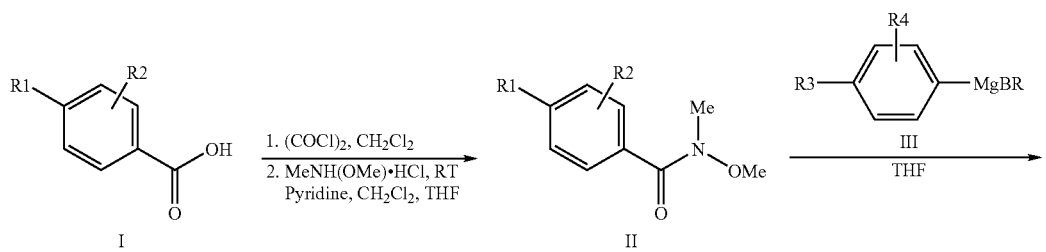

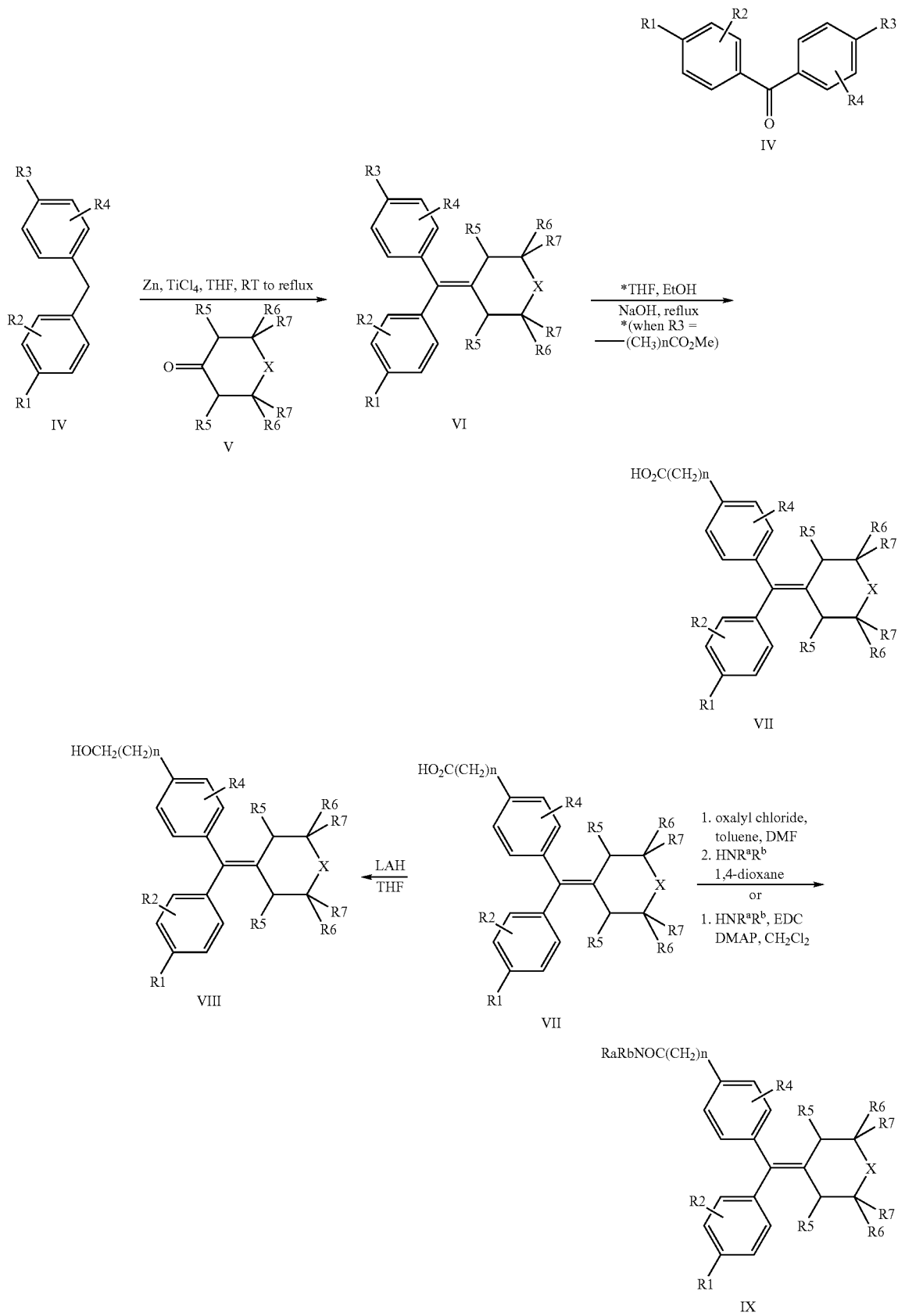

The symmetric cycloalkylidene diphenylethylene VI can be prepared via a McMurry coupling reaction between a benzophenone IV and a ketone V as illustrated in Scheme 1. For McMurry reaction conditions, see Mukaiyama et al., *Chem. Lett.* (1973), 1041; Lenoir, *Synthesis*, (1977), 553; Lenoir and Burghard, *J. Chem. Res. (S)* (1980), 396; McMurry, *Chem. Rev.* (1989), 89, 1513-1524; McMurry, *Acc. Chem. Res.* (1983) 16, 405-511; and S. Gauthier et al., *J. Org. Chem.*, (1996), 61, 3890-3893, each herein incorporated by reference with regard to such teaching. Ketone V is either commercially available or may be prepared by synthetic methods appreciated by those skilled in the art. Benzopheone IV is either commercially available or may be prepared from a Friedel-Crafts acylation between an acid chloride and an anisole derivative using methods appreciated by those skilled in the art. For Friedel-Crafts reaction conditions, see *Friedel-Crafts and Related Reactions*, G. A. Olah, ed., Vol 3, Pt 1, pp 1-382, J. Wiley and Sons, New York (1964); G. A. Olah, *Friedel-Crafts Chemistry*, Wiley Interscience, New York, (1973); and Larock, R. C., *Comprehensive Organic Transformations*, VCH Publishers, New York, 1989, each herein incorporated by reference with regard to such teaching. Alternatively, benzophenones such as IV can be prepared by treatment of a Weinreb Amide II derivative with an aryl Grignard reagent III, see Tetrahedron Letters, 22(39), 3815-18; 19), herein incorporated by reference with regard to such teaching.

Further elaboration of the R3 substituent of VI can be carried out. For example, when R3 is an ester, saponification will yield the carboxylic acid VII and treatment with a reducing agent such as LAH yields the corresponding alcohol VII. Acid VII can also be converted to a carboxamide IX. Treatment of acid (VII) with an amine in the presence of a coupling agent such as EDC and DMAP in dichloromethane provides amide IX. Alternatively, acid VII can be converted to the acid chloride using oxalyl chloride and DMF in toluene followed by treatment of the crude acid chloride with an amine to give amide IX. For conversion of carboxylic acids to amides, see Larock, R. C., *Comprehensive Organic Transformations*, VCH Publishers, New York, 1989, herein incorporated by reference with regard or such teaching.

Scheme 2
General Route to Cycloalkylidene Diphenylethylenes
Acrylic Acids and Acrylamides

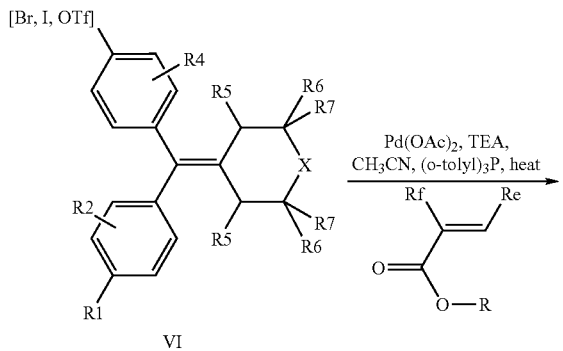

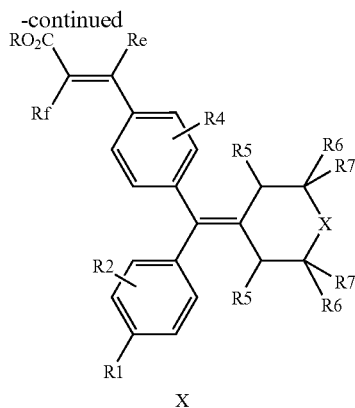

X $\xrightarrow{\text{Ester Hydrolysis}}$

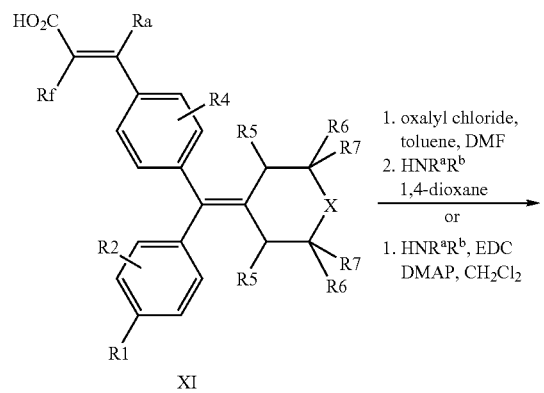

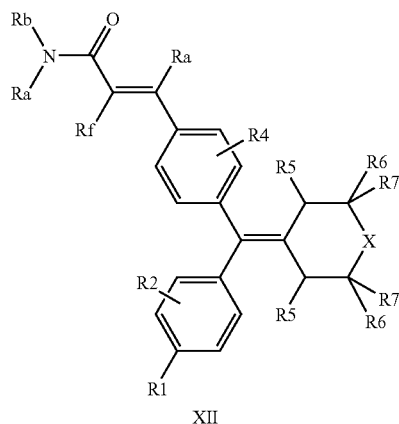

Acrylic acid XI can be prepared in two steps from compound VI as illustrated in Scheme 2. Heck coupling of VI with an acrylate ester (wherein the depicted R is a suitable alkyl group (e.g. methyl, ethyl, tert-butyl) provides X. For reviews of the Heck reaction, see Heck, *Acc. Chem. Res.* (1979), 12, 146-151; Heck, *Pure Appl. Chem.* (1978), 50, 691-701; R. F. Heck, *Palladium Reagents in Organic Syntheses*, Academic Press, New York (1985), 179-321, Bender, Stakem, and Heck, *J. Org. Chem.* (1982), 47, 1278; Spencer, *J. Organomet. Chem.* (1983), 258, 101; and Brase, Stefan; De Meijere, Armin. Palladium-catalyzed Coupling of Organyl Halides to Alkenes—the Heck Reaction, *Metal-Catalyzed Cross-Coupling Reactions* (1998), 99-166, Publisher: Wiley-VCH Verlag GmbH, Weinheim, Germany, each herein incorporated by reference with regard to such teaching. Ester hydrolysis of X provides acrylic acid XI.

The analogue of XI where $R^1$ is F can be prepared by the methods illustrated in Schemes 1 and 2 by employing (4-bromophenyl)(4-fluorophenyl)methanone which can be prepared by methods described in the literature (for example, Z. Vejdelek et al., *Collect. Czech. Chem. Commun.*, (1984), 49(11), 2649-2660, herein incorporated by reference with regard to such teaching).

Acrylic acid XI can be converted to an amide as illustrated in Scheme 2. Treatment of acrylic acid (XI) with an amine in the presence of a coupling agent such as EDC and DMAP in dichloromethane provides amide XII. Alternatively, acrylic acid XI can be converted to the acid chloride using oxalyl chloride and DMF in toluene followed by treatment of the crude acid chloride with an amine to give amide XII. For conversion of carboxylic acids to amides, see Larock, R. C., *Comprehensive Organic Transformations*, VCH Publishers, New York, 1989, herein incorporated by reference with regard to such teaching.

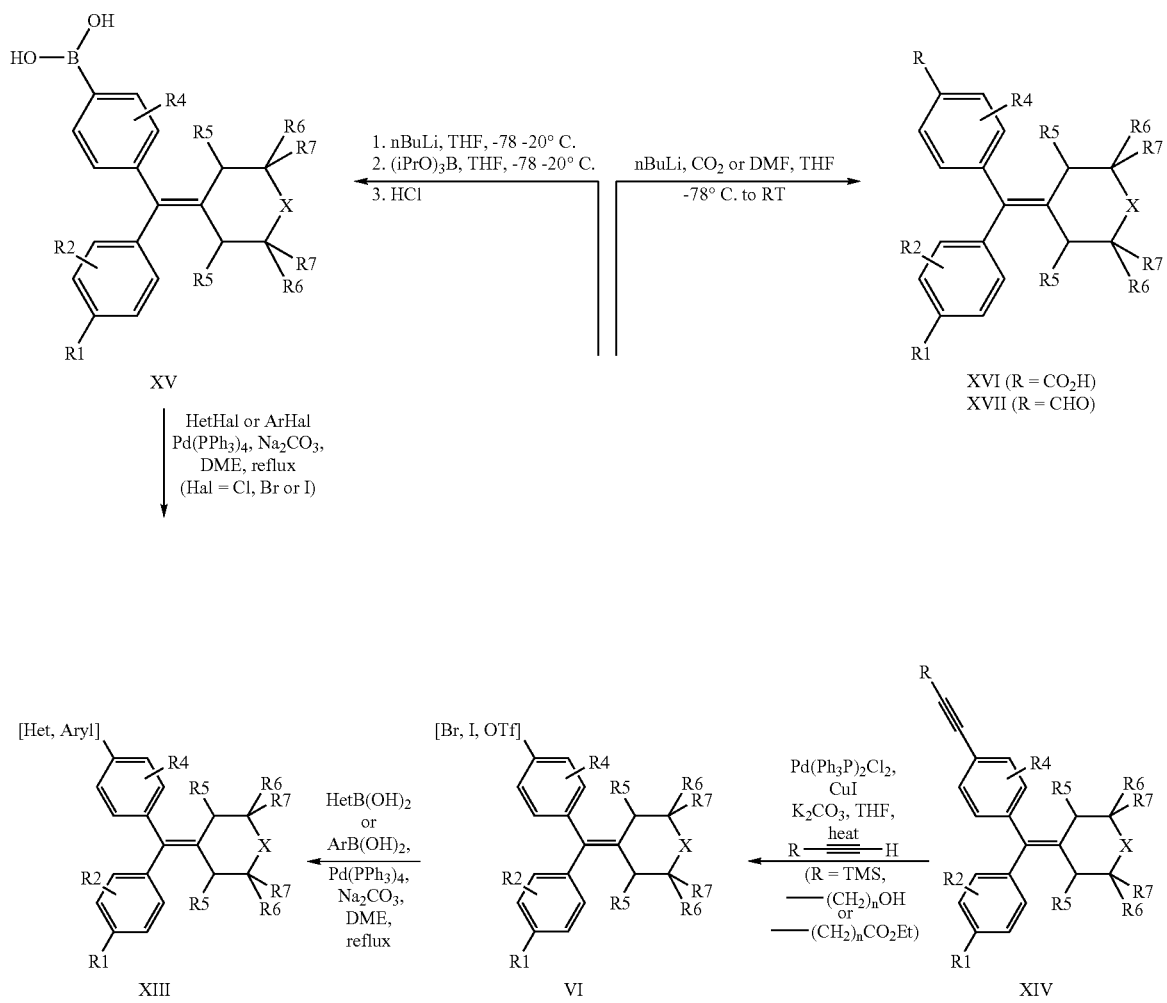

Cycloalkylidene VI is a versatile intermediate that can be used to prepare a variety of compounds as illustrated in Scheme 3.

Coupling of VI with an aryl or heteroaryl-substituted boronic acid using Suzuki reaction conditions provides XIII. For reaction conditions of the Suzuki coupling reaction, see, Miyaura, N., Suzuki, A. *Chem. Rev.* 1995, 95, 2457-2483; Suzuki, A., *J. Organometallic Chem.* (1999), 576, 147-168; and Suzuki, A. in *Metal-catalyzed Cross-coupling Reactions*, Diederich, F., and Stang, P. J., Eds.; Wiley-VCH: New York, (1998), pp. 49-97, each herein incorporated by reference with regard to such teaching. Alternatively, XIII can be prepared by Suzuki-coupling of boronic acid XV with an aryl or heteroaryl halide. Boronic acid XV can be prepared by metal-halogen exchange of VI using butyllithium followed by treatment of the resulting organolithium with triisopropyl borate and subsequent hydrolysis. For reaction conditions, see X. Deng et al., *J. Org. Chem.*, (2002), 67(15), 5279-5283 and P. J. Hajduk et al., *J. Amer. Chem. Soc.*, (1997), 119(25), 5818-5827, each herein incorporated by reference with regard to such teaching.

Metal-halogen exchange of VI using butyl lithium followed by treatment with carbon dioxide or DMF provides benzoic acid XVI and benzaldehyde XVII respectively. For reaction conditions, see T. Mizuno et al., *Tetrahedron*, (1999), 55(31), 9455-9468; J. W. Lampe et al., *J. Med. Chem.*, (2002), 45(12), 2624-2643; R. G. Leenders et al., *Bioorg. Med. Chem.* (1999), 7(8), 1597-1610; and A. Endo et al., *J. Amer. Chem. Soc.*, (2002), 124(23), 6552-6554, each herein incorporated by reference with regard to such teaching.

Amides can be prepared from XVI by methods illustrated in Scheme 2. Benzaldehyde XVII can be converted to acrylate ester X via Wadsworth-Emmons chemistry (For Wadsworth-Emmons chemistry, see J. Boutagy and R. Thomas *Chem. Rev.* (1974), 74, 87-99; Wadsworth, *Org. React* (1977), 25, 73-253; Y. Momose, et al., *J. Med. Chem.*, (2002), 45(7), 1518-1534; and S. D. Bull et al., *J. Chem. Soc. Perkin Trans I*, (2001), 23, 3112-3121, each herein incorporated by reference with regard to such teaching.

Sonagashira coupling of VI with a propiolate ester, propiolate alcohol or (trimethylsilyl)acetylene provides aromatic alkyne XIV. See Campbell, I. B. "*The Sonagashira Cu—Pd-catalyzed alkyne coupling reaction*" in *Organocopper Reagents*, Taylor, Richard J. K. ed., (1994), 217-35. Publisher: IRL Press, Oxford, UK; G. C. Nwokogu et al., *J. Org. Chem.*, (1994), 59(9), 2506-2510; and A. P. Kozikowski *J. Med. Chem.* (2000), 43(6), 1215-1222 and T. Eckert and J. Ipaktschi *Synth. Commun.* (1998), 28, 327-336, each herein incorporated by reference with regard to such teaching. Compound XIV can be further treated to prepare additional new analogues. For example, when the depicted R group is TMS, the TMS group can be removed to yield the corresponding terminal acetylene. When the depicted R group is an ester, hydrolysis or reduction affords the receptive corresponding acid or alcohol (see conditions illustrated in Scheme 1).

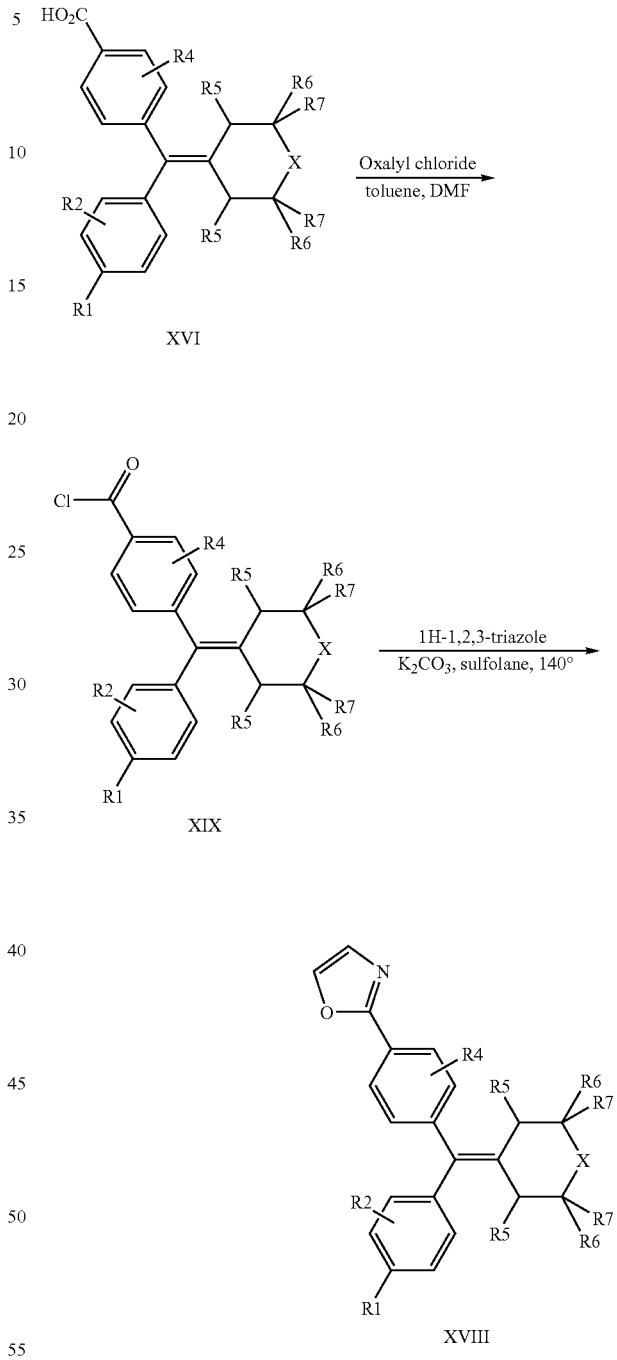

Scheme 4
General Synthesis of Cycloalkylidene Diphenylethylene Oxazole

The 2-substituted oxazole XVIII is prepared in two steps from benzoic acid XVI as illustrated in Scheme 4. Treatment of XVI with oxalyl chloride gives acid chloride XIX which is then treated with 1H-1,2,3-triazole in the presence of base to provide oxazole XVIII. For reaction conditions leading to the formation of an oxazole from either an aromatic acid chloride or benzamide, see Murugesan, N. et al., *J. Med. Chem.* (2000), 43, 3111-3117, herein incorporated by reference with regard to such teaching.

Scheme 5
General Synthesis of Cycloalkylidene Diphenylethylene Sulfonamides and Amides

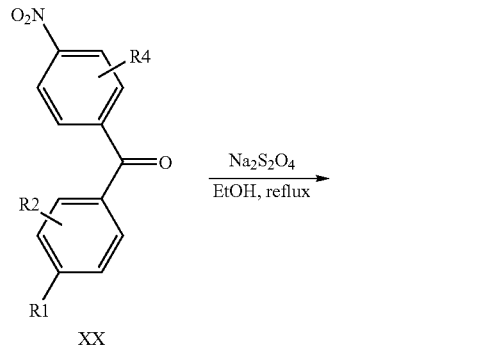

XX

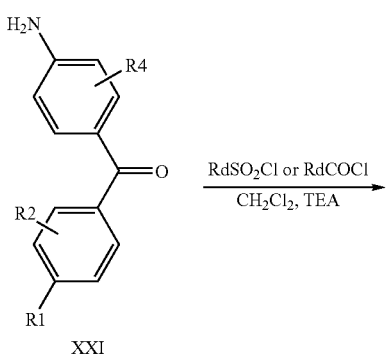

XXI

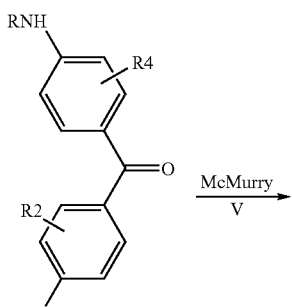

XXII (R = SO₂Rd)
XXIII (R = CORc)

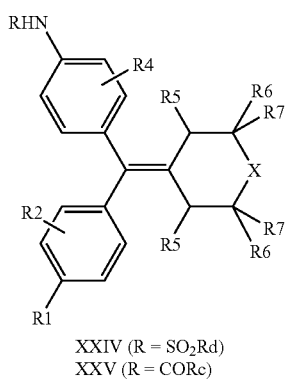

XXIV (R = SO₂Rd)
XXV (R = CORc)

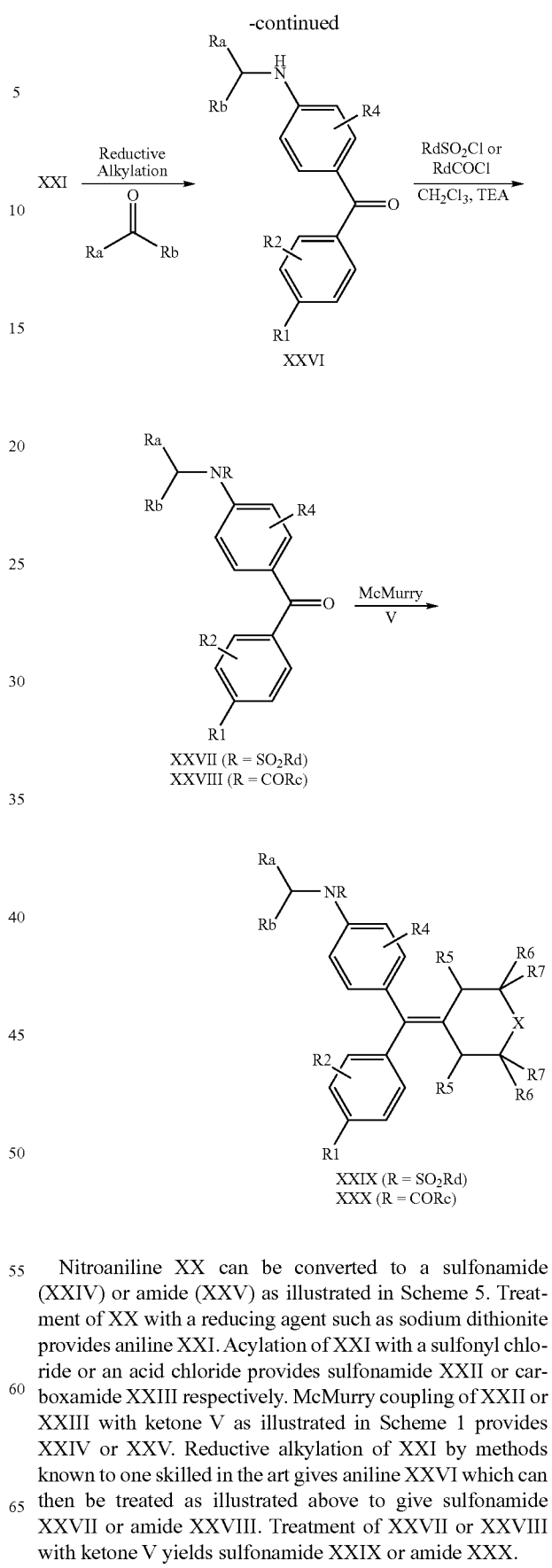

XXVI

XXVII (R = SO₂Rd)
XXVIII (R = CORc)

XXIX (R = SO₂Rd)
XXX (R = CORc)

Nitroaniline XX can be converted to a sulfonamide (XXIV) or amide (XXV) as illustrated in Scheme 5. Treatment of XX with a reducing agent such as sodium dithionite provides aniline XXI. Acylation of XXI with a sulfonyl chloride or an acid chloride provides sulfonamide XXII or carboxamide XXIII respectively. McMurry coupling of XXII or XXIII with ketone V as illustrated in Scheme 1 provides XXIV or XXV. Reductive alkylation of XXI by methods known to one skilled in the art gives aniline XXVI which can then be treated as illustrated above to give sulfonamide XXVII or amide XXVIII. Treatment of XXVII or XXVIII with ketone V yields sulfonamide XXIX or amide XXX.

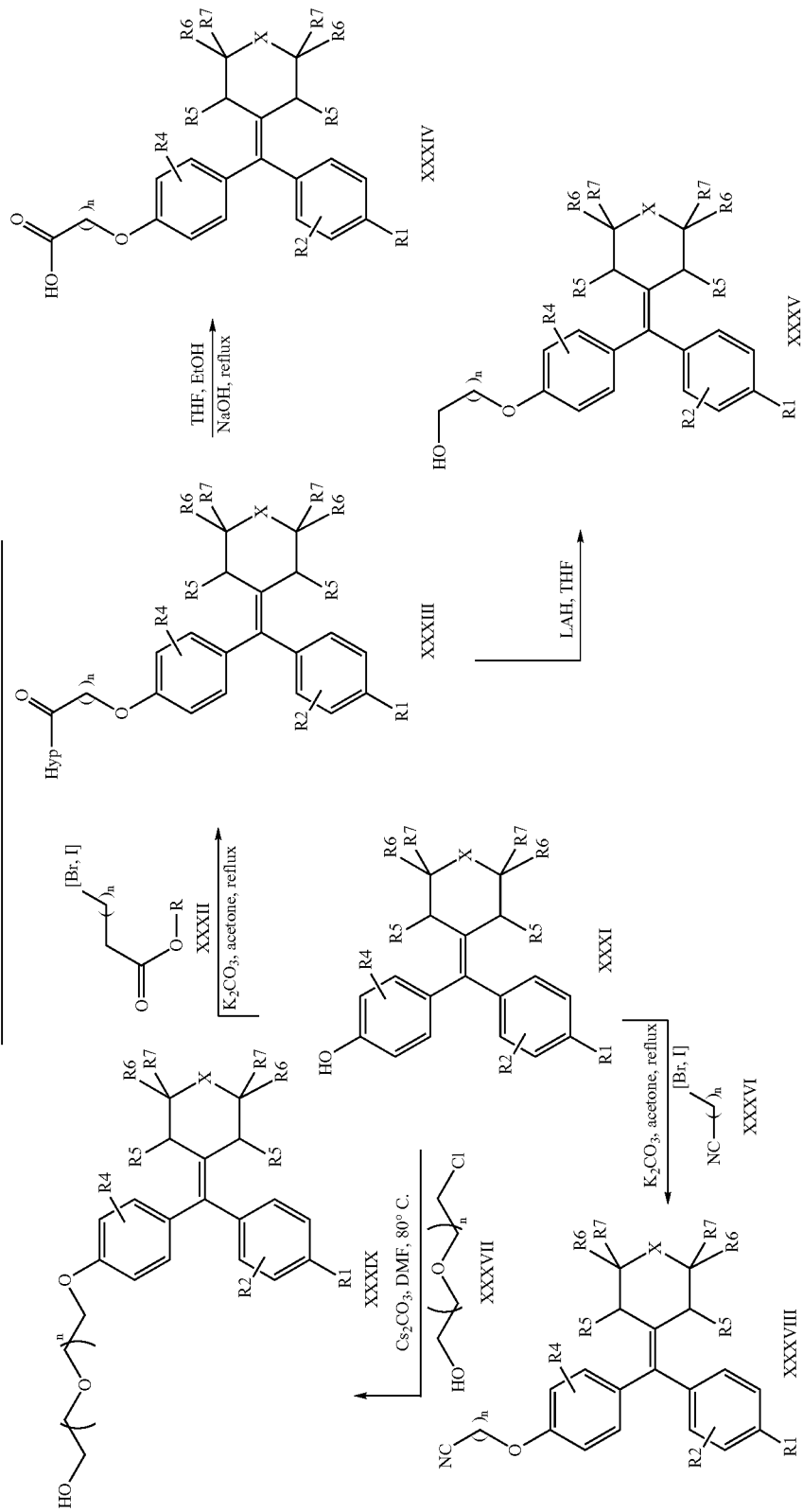

A variety of alkyl derivatives can be prepared in two or three steps via o-alkylation of phenol XXXI as illustrated in Scheme 6. As described above, compounds similar to XXXI can be prepared by McMurry coupling between an appropriately substituted benzophenone and ketone V. For McMurry reaction conditions, see references cited for Scheme 1 above. O-Alkylation of XXXI can be accomplished in the presence of a suitable base and a haloester such as XXXII (wherein the depicted R group is a suitable alkyl group, e.g. methyl, ethyl, tert-butyl, etc.). Saponification of the resulting ester XXXIII provides acid XXXIV. Conversion of ester XXXIII to the alcohol XXXV can be effected by treatment with a reducing agent such as lithium aluminum hydride (LAH). Similarly, phenol XXXI can be alkylated with a haloacetonitrile XXXVI or haloalcohol XXXVII to yield compounds XXX-VIII and XXXIX respectively. For examples of related phenol alkylation reactions see Rubin, V. et al., *Bioorganic & Med. Chem.* (2001), 9, 1579-1586, herein incorporated by reference with regard to such teaching.

EXAMPLES

The following specific examples are included as illustrations and are not to be construed as limiting the scope of the present invention. For ease of reference, certain compounds are referred to herein using a bolded number. The use of this shorthand reference is meant to refer to the compound generally rather than the specific compound synthesized.

Example 1 (3)

(2E)-3-{4-[Cycloheptylidene(phenyl)methyl]phenyl}prop-2-enoic Acid (3)

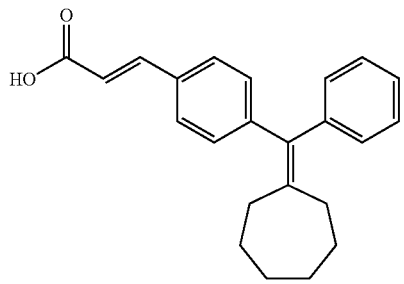

Step 1: [(4-Bromophenyl)(phenyl)methylene]cycloheptane (1)

To a stirred suspension of Zn powder (4.80 g, 73.5 mmol) and THF (100 mL) under $N_2$ was added $TiCl_4$ (3.9 mL, 35.7 mmol), dropwise. The resulting yellow suspension was stirred at RT for 45 min followed by reflux for 2.5 h. A solution of cycloheptanone (3.42 g, 30.6 mmol) and 4-bromobenzophenone (2.54 g, 9.75 mmol) in THF (40 mL) was added dropwise to the refluxing reaction over 15 min. After 2 h the reaction was cooled to RT and then quenched by sequential dropwise addition of water (75 mL) and 10% aqueous $Na_2CO_3$ (75 mL). The mixture was stirred overnight at RT then diluted with EtOAc (300 mL) and filtered through a celite pad. The celite pad was rinsed with EtOAc (250 mL) and the colorless filtrates transferred to a separatory funnel. The organic fraction was washed with brine (300 mL), dried ($Na_2SO_4$) and concentrated to 6.50 g of a colorless oil. The oil was purified by column chromatographed on silica gel (150 g) with hexanes followed by 2% EtOAc:hexanes and the product 1 isolated as a colorless oil that solidified on standing (2.54 g, 76%). $^1$H NMR (300 MHz, DMSO-$d_6$): δ 1.59 (s, 8H), 2.27 (br s, 4H), 7.15-7.39 (m, 7H), 7.55 (d, J=8.3 Hz, 2H).

Step 2: tert-Butyl (2E)-3-{4-[cycloheptylidene(phenyl)methyl]phenyl}prop-2-enoate (2)

A stirred suspension of 1 (0.77 g, 2.24 mmol), TEA (1.86 mL, 13.4 mmol), t-butylacrylate (1.96 mL, 13.4 mmol), $Pd(OAc)_2$ (0.12 g, 0.50 mmol), P(o-tolyl)$_3$ (0.28 g, 0.90 mmol) and $CH_3CN$ were stirred at reflux under $N_2$. Heating was discontinued after 2 h and the reaction diluted with EtOAc (50 mL) and water (50 mL). The mixture was filtered through a celite pad and the filtrate transferred to a separatory funnel. The organic fraction was washed with 50 mL brine (50 mL), dried ($MgSO_4$), filtered and concentrated to 1.39 g of an amber oil. The crude product was purified by flash chromatography on silica gel with a hexanes to 5% EtOAc:hexanes gradient. The product, 2, was isolated as a colorless, viscous oil (900 mg, 100%). $^1$H NMR (300 MHz, DMSO-$d_6$): δ 1.52 (s, 9H), 1.59 (s, 8H), 2.31 (br, 4H), 6.51 (d, J=16 Hz, 1H), 7.19-7.38 (m, 7H), 7.56 (d, J=16 Hz, 1H), 7.66 (d, J=8.1 Hz, 2H).

Step 3: (2E)-3-{4-[Cycloheptylidene(phenyl)methyl]phenyl}prop-2-enoic acid (3)

To a stirring solution of 2 (0.77 g, 2.24 mmol) in $CH_2Cl_2$ (25 mL) at 0° C., was added, drop wise, TFA over 15 min. The pale yellow, reaction was stirred at 0° C. for 1 h then allowed to stand at RT for 15 min. The reaction was concentrated to a viscous oil, redissolved in $CH_2Cl_2$ (20 mL) and reconcentrated to a gummy solid. The crude product was crystallized from ether/hexanes to afford the title compound (3) as a white solid (0.30 g, 41%). $^1$H NMR (300 MHz, DMSO-$d_6$): δ 1.59 (s, 8H), 2.29 (br s, 4H), 6.52 (d, J=16 Hz, 1H), 7.15-7.39 (m, 7H), 7.59 (d, J=16 Hz, 1H), 7.66 (d, J=8.3 Hz, 2H), 12.41 (s, 1H). LRMS (APCI): m/z 433 (M+H)$^+$. Anal. Calcd for $C_{23}H_{24}O_2$: C, 83.07; H, 7.30. Found: C, 82.73; H, 7.25.

Example 2 (4)

(2E)-3-{4-[Cycloheptylidene(phenyl)methyl]phenyl}prop-2-enamide (4)

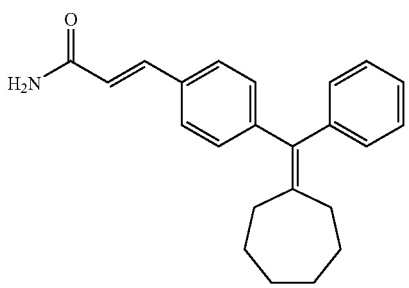

A suspension of [(4-Bromophenyl)(phenyl)methylene]cycloheptane (1) (0.50 g, 1.47 mmol), TEA (1.21 mL, 8.71 mmol), acrylamide (0.62 g, 8.73 mmol), $Pd(OAc)_2$ (0.080 g, 0.36 mmol), P(o-tolyl)$_3$ (0.19 g, 0.63 mmol) and $CH_3CN$ was stirred at reflux under $N_2$. After 2 h heating was discontinued and the reaction diluted with EtOAc (50 mL) and water (50 mL). The mixture was filtered through a celite pad and the filtrate transferred to a separatory funnel. The organic fraction was washed with brine (50 mL), dried (MgSO$_4$), filtered and concentrated to an amber oil. This oil was purified by column chromatography on silica gel (50 g) using a hexanes to 25% EtOAc:hexanes to 100% EtOAc gradient to afford a pale yellow solid. Trituration of the solid with EtOAc (25 mL) yielded 164 mg (33%) of the title compound (4) as a white solid. $^1$H NMR (300 MHz, DMSO-d$_6$): δ 1.54 (s, 8H), 2.24 (br s, 4H), 6.55 (d, J=15.9 Hz, 1H), 7.07 (br, 1H), 7.14-7.20 (m, 7H), 7.25 (d, J=15.9 Hz, 1H), 7.49 (d, J=8.1 Hz, 2H), 7.50 (br, 1H). LRMS (APCI): m/z 332 (M+H)$^+$. Anal. Calcd for C$_{23}$H$_{25}$NO.0.1H$_2$O: C, 82.67; H, 7.63; N, 4.19. Found: C, 82.75; H, 7.56; N, 4.20.

Example 3 (6)

2-({4-[Phenyl(3,3,5,5-tetramethylcyclohexylidene)methyl]phenyl}oxy)ethanol (6)

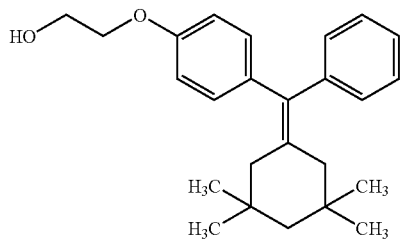

Step 1: {4-[(2-Hydroxyethyl)oxy]phenyl}(phenyl)methanone (5)

To a solution of 4-hydroxybenzophenone (6.0 g, 29.7 mmol) in acetone (50 mL) were added K$_2$CO$_3$ (12.3 g, 89.0 mmol) and 2-chloroethanol (4.0 mL, 59.3 mmol), followed by addition of NaI (4.50 g, 29.7 mmol). The reaction mixture was refluxed under nitrogen overnight. The mixture was cooled to room temperature. The white solid was filtered off and washed with acetone (100 mL). The filtrate was concentrated to a brown oil residue with some white solid. EtOAc (200 mL) was added, the white solid was filtered off and then washed with 50 mL of EtOAc. The filtrate was washed with 1 N NaOH, water, brine and dried over Na$_2$SO$_4$. Concentration afforded a pale yellow oil which was further purified by chromatography on a silica gel column eluted with a gradient from hexanes to 60% EtOAc:hexanes to give 5 as a white solid (1.52 g, 21%). $^1$H NMR (400 MHz, CDCl$_3$): δ 4.00-4.05 (m, 2H), 4.15-4.20 (m, 2H), 6.98 (d, J=8.7 Hz, 2H), 7.45-7.50 (m, 2H), 7.55-7.60 (m, 1H), 7.75 (d, J=7.1 Hz, 2H), 7.83 (d, J=8.8 Hz, 2H).

Step 2: 2-({4-[Phenyl(3,3,5,5-tetramethylcyclohexylidene)methyl]phenyl}oxy)ethanol (6)

To a stirred suspension of Zn (0.65 g, 9.91 mmol) in THF (10 mL) was added TiCl$_4$ (0.55 mL, 4.95 mmol) dropwise. The mixture was refluxed under nitrogen for 2.5 h. After cooling to room temperature, a solution of 5 (0.30 g, 1.24 mmol) and 3,3,5,5-tetramethylcyclohexanone (0.59 g, 3.71 mmol) in THF (17 mL) was added at once. The reaction mixture was refluxed for another 2.5 h. Following cooling to room temperature, the reaction was quenched with 10% K$_2$CO$_3$ (40 mL). The quenched reaction mixture was filtered through a pad of celite and the pad was washed with EtOAc (50 mL). The filtrate was transferred to a separatory funnel, the layers were separated, and the aqueous layer was extracted with EtOAc (50 mL). The organic extracts were combined, washed with brine, dried (Na$_2$SO$_4$) and concentrated to give a pale yellow oil. The residue was further purified by chromatography on a silica gel column eluted with a gradient from hexanes to 20% EtOAc:hexanes to give 6 as a white solid (0.35 g, 78%). mp 131-132° C. $^1$H NMR (400 MHz, CD$_3$OD): δ 0.91 (s, 6H), 0.92 (s, 6H), 1.29 (s, 2H), 1.95 (s, 2H), 1.99 (s, 2H), 3.80-3.85 (m, 2H), 4.00-4.05 (m, 2H), 6.85 (d, J=8.8 Hz, 2H), 7.06 (d, J=8.6 Hz, 2H), 7.10-7.20 (m, 3H), 7.20-7.25 (m, 2H). LRMS (ESI): m/z 365 (M+H)$^+$. Anal. Calcd for C$_{25}$H$_{32}$O$_2$: C, 82.37; H, 8.85. Found: C, 82.11; H, 9.03.

Example 4 (8)

2-{[2-({4-[Phenyl(3,3,5,5-tetramethylcyclohexylidene)methyl]phenyl}oxy)ethyl]oxy}ethanol (8)

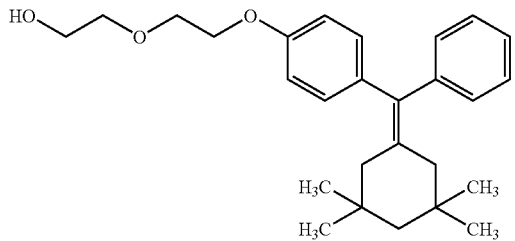

Step 1: [4-({2-[(2-Hydroxyethyl)oxy]ethyl}oxy)phenyl](phenyl)methanone (7)

To a suspension of 4-hydroxybenzophenone (4.0 g, 19.8 mmol) in CH$_3$CN (30 mL) was added K$_2$CO$_3$ (8.20 g, 59.3 mmol). The mixture was refluxed under nitrogen for 1 h. Cooled to room temperature, 2-(2-chloroethoxy)ethanol (4.3 mL, 39.6 mmol) was added, followed by addition of NaI (3.00 g, 19.8 mmol). The reaction mixture was refluxed under nitrogen overnight. The mixture was cooled to room temperature and EtOAc (50 mL) was added. The precipitated white solid was filtered and washed with EtOAc (50 mL). The filtrate was transferred to a separatory funnel and washed with 1 N NaOH, water, brine and dried over Na$_2$SO$_4$. Concentration yielded a yellow oil which was further purified by chromatography on a silica gel column eluted with a gradient from hexanes to 70% EtOAc:hexanes to give 7 as colorless crystals (4.96 g, 88%). mp 31-32° C. $^1$H NMR (400 MHz, CDCl$_3$): δ 3.65-3.75 (m, 2H), 3.75-3.80 (m, 2H), 3.90-3.95 (m, 2H), 4.20-4.25 (m, 2H), 6.99 (d, J=8.8 Hz, 2H), 7.45-7.50 (m, 2H), 7.55-7.60 (m, 1H), 7.70-7.80 (m, 2H), 7.83 (d, J=8.8 Hz, 2H). LRMS (ESI): m/z 287 (M+H)$^+$.

Step 2: 2-{[2-({4-[Phenyl(3,3,5,5-tetramethylcyclohexylidene)methyl]phenyl}oxy)ethyl]oxy}ethanol (8)

To a stirred suspension of Zn (0.59 g, 8.94 mmol) in THF (10 mL) was added TiCl$_4$ (0.50 mL, 4.47 mmol) dropwise. The mixture was refluxed under nitrogen for 2.5 h. Cooled to room temperature, a solution of 7 (0.32 g, 1.12 mmol) and 3,3,5,5-tetramethylcyclohexanone (0.53 g, 3.35 mmol) in THF (15 mL) was added and the reaction mixture was refluxed for another 2.5 h. Cooled to room temperature, the reaction was quenched with 10% K$_2$CO$_3$ (40 mL). The quenched reaction mixture was filtered through a pad of celite and the pad was washed with EtOAc (100 mL). The filtrate was transferred to a separatory funnel, the layers were separated, and the aqueous layer was extracted with EtOAc (50 mL). The combined organic extracts were washed with brine, dried (Na$_2$SO$_4$) and concentrated to a pale yellow oil. The residue was further purified by chromatography on a silica gel column eluted with a gradient from hexanes to 45% EtOAc:hexanes to give 8 as a white solid. Crystallization from 10:1 hexanes:EtOAc yielded colorless needles (0.27 g, 59%). mp 116-117° C. $^1$H NMR (400 MHz, CD$_3$OD): δ0.91 (s, 6H), 0.93 (s, 6H), 1.29 (s, 2H), 1.95 (s, 2H), 1.99 (s, 2H), 3.60-3.65 (m, 2H), 3.65-3.70 (m, 2H), 3.80-3.85 (m, 2H), 4.05-4.15 (m, 2H), 6.85 (d, J=8.6 Hz, 2H), 7.06 (d, J=8.6 Hz, 2H), 7.10-7.20 (m, 3H), 7.20-7.30 (m, 2H). LRMS (ESI): m/z 409 (M+H)$^+$. Anal. Calcd for C$_{27}$H$_{36}$O$_3$: C, 79.37; H, 8.88. Found: C, 79.23; H, 8.95.

Example 5 (11)

({4-[(4-Fluorophenyl)(3,3,5,5-tetramethylcyclohexylidene)methyl]phenyl}oxy)acetic acid (11)

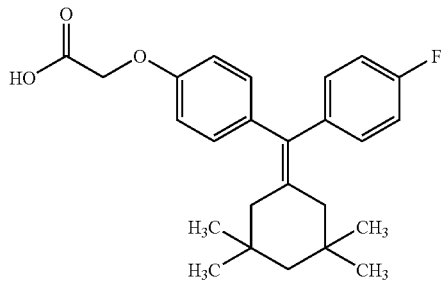

Step 1: 4-[(4-Fluorophenyl)(3,3,5,5-tetramethylcyclohexylidene)methyl]phenol (9)

The coupling procedure described for 1 (example 1, step 1) was employed. A mixture of (4-fluorophenyl)(4-hydroxyphenyl)methanone (4.32 g, 20 mmol), 3,3,5,5-tetramethylcyclohexanone (9.26 g, 60 mmol), Zn (13 g, 200 mmol), TiCl$_4$ (10.9 mL, 100 mmol), and THF (400 mL) was refluxed for 2.5 h. Standard work-up followed by purification afforded 5.450 g (80%) of the title product 9 as a white solid. $^1$H NMR (400 MHz, CDCl$_3$): δ 7.15-7.11 (m, 2H), 7.04 (d, J=8.7 Hz, 2H), 7.00-6.94 (m, 1H), 6.76 (d, J=8.7 Hz, 2H), 4.68 (br s, 1H), 2.0 (s, 2H), 1.96 (s, 2H), 1.31 (s, 2H), 0.95 (s, 6H), 0.94 (s, 6H). LCMS (APCI): m/z 429 (M+H)$^+$.

Step 2: Ethyl ({4-[(4-fluorophenyl)(3,3,5,5-tetramethylcyclohexylidene)methyl]phenyl}(oxy)acetate (10)

To a stirred suspension of 4-[(4-fluorophenyl)(3,3,5,5-tetramethylcyclohexylidene) methyl]phenol 9 (0.339 g, 1.0 mmol), K$_2$CO$_3$ (0.276 g, 2.0 mmol), and acetone (40 mL) was added ethylbromoacetate (0.221 mL, 2.5 mmol) under a nitrogen atmosphere at room temperature. The reaction mixture was refluxed for 6 h, cooled to room temperature and filtered. The filtrate was concentrated under reduced pressure and the crude product purified by flash chromatography on silica gel with hexanes and EtOAc to afford 0.340 g (80%) of compound 10 as a white foam. $^1$H NMR (300 MHz, CDCl$_3$): δ 7.15-7.12 (m, 1H), 7.09 (d, J=8.4 Hz, 2H), 6.98 (d, J=8.7 Hz, 1H), 6.95 (d, J=8.7 Hz, 2H), 6.84 (d, J=8.7 Hz, 2H), 4.61 (s, 2H), 4.29 (q, J=6.90 Hz, 2H), 1.98 (s, 2H), 1.96 (s, 2H), 1.31 (s, 2H), 1.31 (t, J=7.2 Hz, 3H), 0.94 (s, 12H). LCMS (ESI): m/z 447 (M+Na)$^+$.

Step 3: ({4-[(4-Fluorophenyl)(3,3,5,5-tetramethylcyclohexylidene)methyl]phenyl}oxy)acetic acid (11)

A solution of ethyl({4-[(4-fluorophenyl)(3,3,5,5-tetramethylcyclohexylidene)methyl]phenyl}oxy)acetate (10) (0.290 g, 0.68 mmol) in THF/EtOH (1:1, 8 mL) was treated with 1 N NaOH (4 mL) at 70° C. for 1 h. The reaction mixture was acidified with 20% aqueous HCl, and then extracted with EtOAc. The organic layer was washed with brine, dried (Na$_2$SO$_4$), and concentrated under reduced pressure to afford the crude product. The product was purified by flash column chromatography with chloroform and methanol as an eluent to afford 0.250 g (95%) of the title compound 11 as a white solid. $^1$H NMR (300 MHz, DMSO-d$_6$): δ 7.19-7.14 (m, 2H), 7.13 (d, J=9.3 Hz, 2H), 7.07 (d, J=8.4 Hz, 2H), 6.83 (d, J=8.7 Hz, 1H), 6.84 (d, J=8.7 Hz, 2H), 4.63 (s, 2H), 1.93 (s, 2H), 1.88 (s, 2H), 1.27 (s, 2H), 0.90 (s, 12H). LCMS (ESI): m/z 395 (M−H)$^−$.

Example 6 (13)

4-({4-[(4-Fluorophenyl)(3,3,5,5-tetramethylcyclohexylidene)methyl]phenyl}oxy)butanoic acid (13)

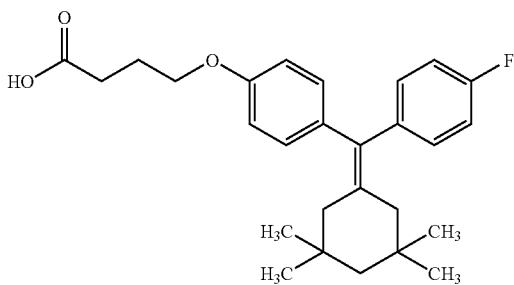

Step 1: Ethyl 4-({4-[(4-fluorophenyl)(3,3,5,5-tetramethylcyclohexylidene) methyl]phenyl}oxy)butanoate (12)

The o-alkylation procedure described for 10 (example 5, step 2) was used. To a stirred suspension of 4-[(4-fluorophenyl)(3,3,5,5 tetramethylcyclohexylidene) methyl]phenol 9 (0.590 g, 1.74 mmol), K$_2$CO$_3$ (0.482 g, 3.5 mmol), and acetone (50 mL) was added ethyl 4-bromobutyrate (0.62 mL, 4.4 mmol) under a nitrogen atmosphere at RT. The reaction mixture was refluxed for 6 h, cooled to RT and filtered. Standard work-up followed by purification afforded 0.712 g (90%) of compound 12 as a white foam. $^1$H NMR (300 MHz, CDCl$_3$): δ 7.14 (d, J=5.7 Hz, 1H), 7.11 (d, J=5.7 Hz, 1H), 7.07 (d, J=8.7 Hz, 2H), 6.98 and 6.95 (dd, J=8.7 Hz, J$_2$=8.7 Hz, 2H), 6.81 (d, J=8.4 Hz, 2H), 4.16 (q, J=7.2 Hz, 2H), 3.99 (t, J=6.00 Hz, 2H), 3.49 (t, J=6.3 Hz, 2H), m, 2H), 2.11 (quint., J=6.30 Hz, 2H), 2.00 (s, 2H), 1.96 (s, 2H), 1.31 (br s, 2H), 1.27 (t, J=7.2 Hz, 3H), 0.95 (s, 6H), 0.94 (s, 6H). LCMS (ESI): m/z 475 (M+Na)$^+$.

Step 2: 4-({4-[(4-Fluorophenyl)(3,3,5,5-tetramethylcyclohexylidene)methyl]phenyl}oxy) butanoic acid (13)

The hydrolysis procedure described for 11 (example 5, step 3) was used. A solution of ethyl 4-({4-[(4-fluorophenyl) (3,3,5,5-tetramethylcyclohexylidene) methyl]phenyl}oxy) butanoate) (12) (0.665 g, 1.47 mmol) in THF/EtOH (1:1, 10 mL) was treated with 1 N NaOH (5 mL, excess) at 70° C. for 1 h. The reaction mixture was cooled and poured into 20% aqueous HCl (40 mL). Standard work-up followed by purification afforded 0.525 g (84%) of the title compound 13 as a white foam. $^1$H NMR (300 MHz, DMSO-$d_6$): δ 12.13 (br s, 1H), 7.15 (d, J=6.6 Hz, 2H), 7.12 (d, J=9.6 Hz, 2H), 7.06 (d, J=8.4 Hz, 2H), 6.85 (d, J=8.4 Hz, 2H), 3.94 (t, J=6.3 Hz, 2H), 2.37 (t, J=7.2 Hz, 2H), 1.93 (s, J=2H), 1.89 (s, 2H), 1.76 (quintet, J=6.3 Hz, 2H), 1.27 (s, 2H), 0.89 (s, 12H). LCMS (ESI): m/z 423 (M–H)$^-$. Anal. Calcd for $C_{27}H_{33}FO_3$, C, 76.39, H, 7.83, F, 4.47. Found: C, 76.30, H, 7.90, F, 4.52.

Example 7 (14)

({4-[(4-Fluorophenyl)(3,3,5,5-tetramethylcyclohexylidene) methyl]phenyl}oxy)acetonitrile (14)

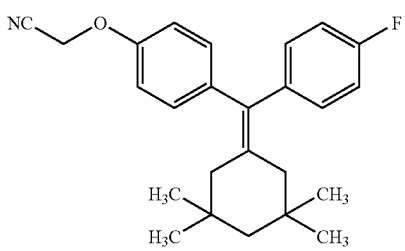

The o-alkylation procedure described for 10 (example 5, step 2) was employed. To a stirred suspension of 4-[(4-fluorophenyl)(3,3,5,5-tetramethylcyclohexylidene) methyl]phenol 9 (0.508 g, 1.5 mmol), $K_2CO_3$ (0.414 g, 3.0 mmol), and acetone (50 mL) was added, under $N_2$ at RT, bromoacetonitrile (0.21 mL, 3.0 mmol). The reaction mixture was refluxed for 4 h, cooled to RT, and filtered. Standard work-up followed by purification afforded 0.410 g (72%) of the title compound 14 as a white foam. mp 100-101° C. $^1$H NMR (300 MHz, CDCl$_3$): δ 7.18-7.11 (m, 4H), 6.99 and 6.97 (dd, J$_1$=8.7 Hz, J$_2$=8.7 Hz, 2H), 6.92 (d, J=8.7 Hz, 2H), 4.76 (s, 2H), 1.98 (s, 2H), 1.97 (s, 2H), 1.32 (s, 2H), 0.96 (s, 12H). LCMS (ESI): m/z 376 (M–H)$^-$. Anal. Calcd for $C_{25}H_{28}FNO$, C, 79.54, H, 7.48; N, 3.71. Found: C, 79.21, H, 7.46; N, 3.73.

Example 8 (15)

2-({4-[(4-Fluorophenyl)(3,3,5,5-tetramethylcyclohexylidene)methyl]phenyl}oxy)ethanol (15)

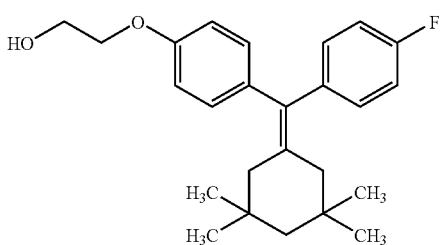

To a solution of ethyl({4-[(4-fluorophenyl)(3,3,5,5-tetramethylcyclohexylidene)methyl]phenyl}oxy)acetate 10 (0.580 g, 1.336 mmol) in anhydrous THF (25 mL) was added LiAlH$_4$ (3.4 mL, 3.42 mmol, 1.0 M solution in THF) dropwise under $N_2$ atmosphere at room temperature. The resultant solution was stirred at RT for 0.5 h. The reaction mixture was quenched with EtOAc (10 mL) and continued the stirring for an additional 10 min. Reaction mixture was poured into 15% aqueous HCl (50 mL) and then extracted with EtOAc (4×30 mL). The combined organic layer was washed with brine (1×30 mL), dried (Na$_2$SO$_4$), and concentrated under reduced pressure to afford the crude product. The product was purified by silica gel column chromatography using hexanes: EtOAc (19:1 to 4:1) as an eluent to afford 0.41 g (79%) of the title compound (15) as white foam. $^1$H NMR (400 MHz, DMSO-$d_6$): δ 7.16-7.06 (m, 4H), 7.03 (d, J=8.4 Hz, 2H), 6.84 (d, J=6.4 Hz, 2H), 4.83 (t, J=5.6 Hz, 1H), 3.92 (t, J=5.2 Hz, 2H), 3.67 (q, J$_1$=10.8 Hz, J$_2$=5.2 Hz, 2H), 1.90 (s, 2H), 1.86 (s, 2H), 1.24 (s, 2H), 0.87 (s, 6H), 0.87 (6H). LCMS (APCI): m/z 405 (M+Na)$^+$.

Example 9 (18)

(2E)-3-{4-[Phenyl(3,3,5,5-tetramethylcyclohexylidene)methyl]phenyl}-2-propenoic acid (18)

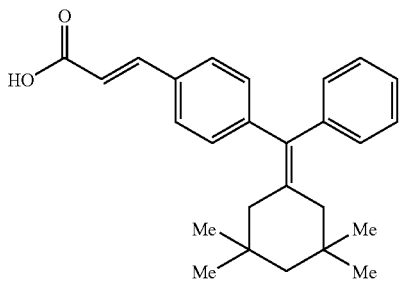

Step 1. 1-Bromo-4-[phenyl(3,3,5,5 tetramethylcyclohexylidene)methyl]benzene (16)

A stirred suspension of Zn dust (3.76 g, 57.5 mmol), 3,3,5,5-tetramethyl cyclohexanone (2.95 g, 19.2 mmol), 4-bromobenzophenone (5.00 g, 19.15 mmol) and anhydrous THF (100 mL) under $N_2$ was cooled to –10° C. and a 1 M solution of TiCl$_4$ in toluene (30 mL) added, dropwise, over 10 min. The temperature was maintained below 0° C. during the addition. After addition was complete the reaction was allowed to warm to RT and then heated at 90° C. for 2 h. The reaction was cooled to –10° C. and concentrated HCl (15 mL) added dropwise followed by water (15 mL). After stirring 30 min, EtOAc (100 mL) was added and the pale yellow 2-phase mixture washed with water (2×75 mL) and brine (1×75 mL) then dried (MgSO$_4$) and concentrated to 8.26 g of a pale yellow oil. The crude oil is purified by column chromatography on 250 g silica gel with 2% EtOAc/hexanes to afford 4.17 g (58%) of the title compound (16) as a white solid. $^1$H-NMR indicated that the product (16) was contaminated with ~8% of an impurity consistent with the pinacol intermediate formed during the McMurry reaction. $^1$H NMR (400 MHz, DMSO-$d_6$): δ 7.46 (d, J=8.3 Hz, 2H), 7.28 (t, J=7.5 Hz, 2H), 7.04-7.19 (m, 5H), 1.87 (s, 4H), 1.24 (s, 2H), 0.87 (s, 6H), 0.86 (s, 6H).

Step 2: Ethyl (2E)-3-{4-[phenyl(3,3,5,5-tetramethylcyclohexylidene)methyl]phenyl}-2-propenoate (17)

A yellow solution of 16, Et$_3$N, ethyl acrylate and dichlorobis(triphenylphosphine) palladium(II) in DMF (25 mL, anhydrous, Aldrich) was stirred overnight under $N_2$ at 110° C. After 16 h the reaction was allowed to cool to RT, filtered, and the filtrate diluted with ether (100 mL) and water (100 mL). The ether layer was rinsed with water (2×75 mL) and brine (1×74 mL) then dried (MgSO$_4$) and concentrated to 5.75 g of a yellow solid. The crude product was purified first by column chromatography on 250 g silica gel with 2% EtOAc/hexanes to yield 6.22 g of an impure white solid. Crystallization from hexanes (~100 mL) afforded 2.39 g (55%) of the title compound 17 as a crystalline white solid. $^1$H NMR (400 MHz, DMSO-d$_6$): δ 7.63 (d, J=8.0 Hz, 2H), 7.59 (d, J=16.1 Hz, 1H), 7.15-7.30 (m, 7H), 6.56 (d, J=16.1 Hz, 1H), 4.15 (q, J=7.1 Hz, 2H), 1.91 (s, 2H), 1.88 (s, 2H), 1.21-1.25 (m, 5H), 0.88 (s, 6H), 0.87 (s, 6H).

Step 3: (2E)-3-{4-[Phenyl(3,3,5,5-tetramethylcyclohexylidene)methyl]phenyl}-2-propenoic acid (18)

A mixture of 17 THF (35 mL) and absolute EtOH (35 mL) was charged with 1 N aqueous NaOH (46 mL) and heated to reflux. After 90 min the reaction was cooled to room temperature. The reaction was diluted with 1 N aqueous HCl (55 mL) and EtOAc (100 mL). The organic fraction iwa washed with water (2×75 mL) and brine (1000 mL) then dried (MgSO$_4$) and concentrated to a white solid. This solid was triturated with hexane (25 mL) and recrystallized from CH$_3$CN (100 mL) to yield: 1.87 g (84%) of the title compound 18 as a white solid. $^1$H NMR (400 MHz, DMSO-d$_6$): δ 12.35 (s, 1H), 7.59 (d, J=8.2 Hz, 2H), 7.53 (d, J=15.9 Hz, 1H), 7.15-7.31 (m, 7H), 6.45 (d, J=15.9 Hz, 1H), 1.91 (s, 2H), 1.89 (s, 2H), 1.26 (s, 2H), 0.88 (s, 6H), 0.87 (s, 6H). LCMS (ESI): m/z 373 (M−H)$^-$.

Example 10 (21)

4-[Phenyl(3,3,5,5-tetramethylcyclohexylidene)methyl]benzoic acid (21)

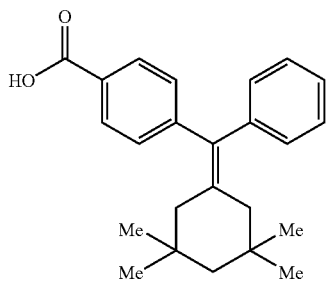

Step 1: Methyl 4-(phenylcarbonyl)benzoate (19)

A stirring solution of MeOH, 4-benzoylbenzoic acid and thionyl chloride was refluxed for 7 h under a nitrogen atmosphere. The reaction was cooled to RT and a white solid precipitated. The mixture was refrigerated overnight then filtered, rinsed with ice chilled MeOH and air-dried to yield 6.10 g (64%) of the title compound 19 as a white solid. $^1$H NMR (400 MHz, DMSO-d$_6$): δ8.09 (d, J=8.2 Hz, 2H), 7.85 (d, J=8.1 Hz, 2H), 7.54-7.74 (m, 5H), 3.88 (s, 3H).

Step 2: Methyl 4-[phenyl(3,3,5,5-tetramethylcyclohexylidene)methyl]benzoate (20)

A stirred suspension of Zn dust (2.45 g, 37.5 mmol), 3,3,5,5-tetramethylcyclohexanone (1.93 g, 12.5 mmol), 19 (3.00 g, 12.5 mmol) and THF (100 mL) under N$_2$ was cooled to −10° C. and a 1 M solution of TiCl$_4$ in toluene (19.5 mL) was added, dropwise, over 10 min. After addition was complete the reaction was allowed to warm to room temperature and then heated at 90° C. for 7 h. The reaction was cooled to room temp and then chilled to −10° C. and concentrated HCl (15 mL) added dropwise followed by water (15 mL). The dark reaction turns a pale purple. EtOAc (60 mL) was added and the mixture washed with water (2×60 mL) and brine (1×60 mL) then dried (MgSO$_4$) and concentrated to 5.1 g of a pale yellow oil. The crude product was purified by column chromatography on 200 g silica gel with a 100% hexanes to 2% EtOAc/hexanes gradient to afford 2.84 g of a white solid which was recrystallized from hexanes. Yield: 0.95 g (21%) of the title compound 20 which was contaminated with ~5% of the pinacol intermediate. $^1$H NMR (400 MHz, DMSO-d$_6$): δ 7.87 (d, J=8.2 Hz, 2H), 7.15-7.31 (m, 7H), 3.80 (s, 3H), 1.89 (s, 2H), 1.86 (s, 2H), 1.25 (s, 2H), 0.87 (s, 6H), 0.86 (s, 6H). Anal. Calcd for C$_{25}$H$_{30}$O$_2$: C, 82.80; H, 8.36. Found: C, 82.94; H, 8.51.

Step 3: 4-[Phenyl(3,3,5,5-tetramethylcyclohexylidene)methyl]benzoic acid (21)

A mixture of 20, THF (15 mL), EtOH (15 mL) is charged with 1 N aqueous NaOH (20 mL) and heated to reflux. After 4 h the reaction was allowed to cool to room temperature and then diluted with 1 N aqueous HCl (30 mL) and EtOAc (50 mL). The organic fraction was washed with water (2×40 mL) and brine (40 mL) then dried (Na$_2$SO$_4$). After concentrating, the solid was triturated with hexane (25 mL), filtered and air-dried to afford 770 mg (86%) of the title compound 21 as a white solid. $^1$H NMR (400 MHz, DMSO-d$_6$): δ 12.82 (s, 1H), 7.86 (d, J=8.2 Hz, 2H), 7.16-7.29 (m, 7H), 1.90 (s, 2H), 1.88 (s, 2H), 1.26 (s, 2H), 0.88 (s, 12H). LCMS (ESI): m/z 347 (M−H)$^-$. Anal. Calcd for C$_{24}$H$_{28}$O$_2$: C, 82.69; H, 8.12. Found: C, 82.48; H, 8.14.

Example 11 (22)

3,5-Dimethyl-4-{4-[phenyl(3,3,5,5-tetramethylcyclohexylidene)methyl]phenyl}isoxazole (22)

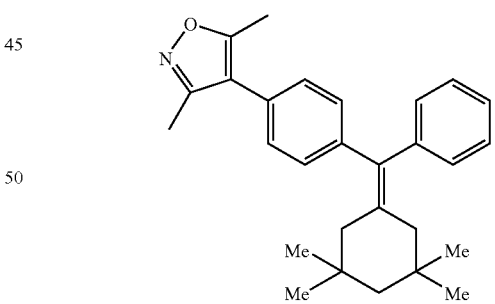

An round-bottomed flask was charged with 16 (192 mg, 0.5 mmol), Pd(Ph$_3$P)$_4$ (58 mg, 0.05 mmol), (3,5-dimethyl-4-isoxazolyl)boronic acid (141 mg, 1.0 mmol), 2 N aqueous Na$_2$CO$_3$ (0.5 mL, 1 mmol), and THF (5 mL). The reaction mixture was refluxed for 18 h. The mixture was cooled to RT, diluted with EtOAc (100 mL), and then the mixture was washed with H$_2$O (1×25 mL), brine (1×25 mL), dried over Na$_2$SO$_4$, filtered, and concentrated under reduced pressure to afford the crude product, which was purified by flash column chromatography to give 136 mg (68%) of the title product 22 as a white solid. $^1$H NMR (400 MHz, CDCl$_3$): δ 0.94 (s, 6H), 0.97 (s, 6H), 1.31 (s, 2H), 1.97 (s, 2H), 2.01 (s, 2H), 2.28 (s, 3H), 2.41 (s, 3H), 7.32-7.14 (m, 9H). LCMS (APCI): m/z 400 (M+H)+.

Example 12 (23)

1-Methyl-4-{4-[phenyl(3,3,5,5-tetramethylcyclohexylidene)methyl]phenyl}-1H-pyrazole (23)

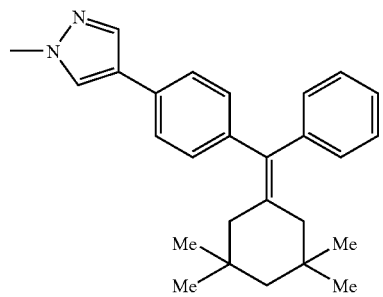

The procedure described for 22 (Example 11) was employed using 16 (192 mg, 0.5 mmol), Pd(Ph₃P)₄ (58 mg, 0.05 mmol), 1-methyl-4-(4,4,5,5-tetramethyl-1,3,2-dioxaborolan-2-yl)-1H-pyrazole (208 mg, 1.0 mmol), 2N aqueous Na₂CO₃ (0.5 mL, 1.0 mmol), and THF (3 mL). The reaction mixture was refluxed for 12 h. Aqueous work-up followed by flash column chromatography afforded 170 mg (88%) of the title product 23 as an off-white solid. ¹H NMR (400 MHz, CDCl₃): δ 7.73 (s, 1H), 7.56 (s, 1H), 7.37 (d, J=8.0 Hz, 2H), 7.26 (d, J=8.8 Hz, 2H), 7.20-7.16 (m, 4H), 3.92 (s, 3H), 2.02 (s, 2H), 1.97 (s, 2H), 1.29 (s, 2H), 0.95 (s, 6H), 0.93 (s, 6H). LCMS (APCI): m/z 385 (M+H)+.

Example 13 (24)

2-{[2-({4-[(4-Fluorophenyl)(3,3,5,5-tetramethylcyclohexylidene)methyl]phenyl}oxy)ethyl]oxy}ethanol (24)

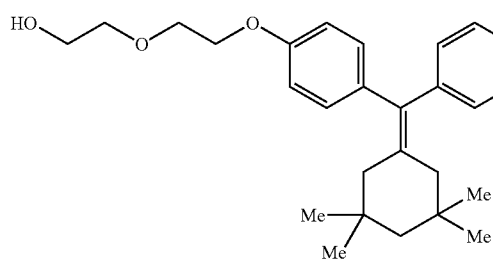

The O-alkylation procedure described for 10 (Example 5, step 2) was followed using 9 (339 mg, 1 mmol), K₂CO₃ (414 mg, 3 mmol), 2-[(2-chloroethyl)oxy]ethanol (0.63 mL, 6 mmol), and acetone (30 mL). The reaction mixture was refluxed for 60 h. The reaction mixture was filtered, concentrated, and purified by column chromatography to give 190 mg (45%) of the title product 24 as a white solid. ¹H NMR (400 MHz, DMSO-d₆): δ 7.16-7.13 (m, 2H), 7.11-7.07 (m, 2H), 7.0 (d, J=8.4 Hz, 2H), 6.84 (d, J=8.4 Hz, 2H), 4.59 (t, J=5.2 Hz, 2H), 4.03 (t, J=4.8 Hz, 2H), 3.70 (t, J=4.4 Hz, 2H), 3.49-3.44 (m, 4H), 1.90 (s, 2H), 1.86 (s, 2H), 1.24 (s, 2H), 0.87 (s, 6H), 0.87 (s, 6H). LCMS (APCI): m/z 427 (M+H)+.

Example 14 (27)

(2E)-3-{4-[(4-Fluorophenyl)(3,3,5,5-tetramethylcyclohexylidene)methyl]phenyl}-2-propenoic acid (27)

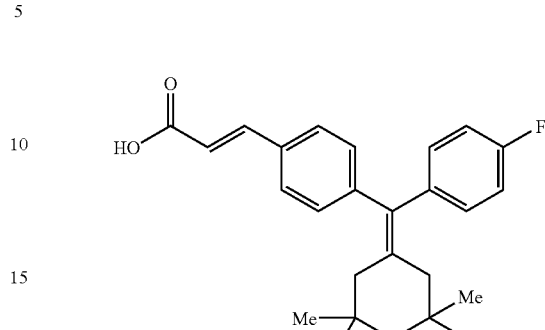

Step 1: 4-[(4-Fluorophenyl)(3,3,5,5-tetramethylcyclohexylidene)methyl]phenyl trifluoromethanesulfonate (25)

To a mixture of 9 (1.0 g, 2.95 mmol) and CH₂CO₂ (50 mL) were added, at 5° C. under N₂, Et₃N (1.22 mL, 8.86 mmol), DMAP (36 mg, 0.30 mmol) followed by trifluoromethane sulphonic anhydride (0.99 mL, 5.91 mmol). The reaction mixture was stirred at RT for 2 h and diluted with CH₂Cl₂ (100 mL) and the mixture was washed with H₂O (1×30 mL), brine (1×30 mL), dried over Na₂SO₄, filtered and the filtrate was concentrated to give the crude product. The product was purified by column chromatography to afford 1.06 g (76%) of the title product 25 as a white solid. ¹H NMR (400 MHz, CDCl₃): δ 7.24 (d, J=6.8 Hz, 1H), 7.22-7.17 (m, 3H), 7.12-7.08 (m, 2H), 6.98 (app. t, J=8.4 Hz, 2H), 1.95 (s, 2H), 1.93 (s, 2H), 1.30 (s, 2H), 0.93 (s, 6H), 0.92 (s, 6H). LCMS (APCI): m/z 493 (M+Na)+.

Step 2: 1,1-Dimethylethyl (2E)-3-{4-[(4-fluorophenyl)(3,3,5,5-tetramethylcyclohexylidene)methyl] phenyl}-2-propenoate (26)

Following the Heck coupling procedure described for 17 (example 9, step 2), a mixture of triflate 25 (840 mg, 1.79 mmol), PdCl₂(PPh₃)₂ (125 mg, 0.18 mmol), Et₃N (990 uL, 7.16 mmol), 1,1-dimethylethyl 2-propenoate (1.62 mL, 17.9 mmol), and DMF (5 mL) was stirred at 110° C. for 24 h. The reaction mixture was cooled to RT and diluted with EtOAc (150 mL). The mixture was washed with H₂O (2×40 mL), brine (1×50 mL), dried and then concentrated under reduced pressure to afford the crude product. The crude material was purified by SiO₂ flash column chromatography to give a 2:1 mixture (TLC) of product and starting material favoring the product 26. This mixture was used without further characterization in the next step.

Step 3: (2E)-3-{4-[(4-Fluorophenyl)(3,3,5,5-tetramethylcyclohexylidene)methyl]phenyl}-2-propenoic acid (27)

A mixture of 26 (~700 mg, a mixture obtained from the above) and CH₂Cl₂ (8 mL) was treated with CF₃CO₂H (2 mL) at RT. The reaction mixture stirred at RT under N₂ for 1.5 h and then concentrated under reduced pressure to afford the crude product. The crude material was purified by column chromatography to afford 165 mg of the desired product 27 as a white solid. A portion (350 mg) of the starting triflate 25 was also recovered. Data for 27: $^1$H NMR (400 MHz, CD$_3$OD): δ 7.64 (d, J=16.0 Hz, 1H), 7.52 (d, J=8.0 Hz, 2H), 7.21 (d, J=8.0 Hz, 2H), 7.18 (d, J=5.6 Hz, 1H), 7.16 (d, J=5.6 Hz, 1H), 7.00 (t, J=8.8 Hz, 2H), 6.44 (d, J=16.00 Hz, 1H), 1.99 (s, 2H), 1.97 (s, 2H), 1.31 (s, 2H), 0.93 (s, 12H). LCMS (APCI): m/z 391 (M−H)$^−$.

Example 15 (28)

4-{4-[(4-Fluorophenyl)(3,3,5,5-tetramethylcyclohexylidene)methyl]phenyl}-3,5-dimethylisoxazole (28)

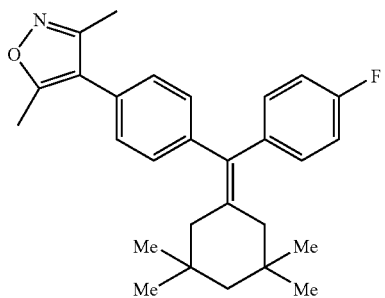

The Suzuki procedure described for 21 was employed using triflate 25 (200 mg, 0.425 mmol), Pd(Ph$_3$P)$_4$ (49 mg, 0.0425 mmol), 2 N aqueous Na$_2$CO$_3$ (425 uL, 0.85 mmol), (3,5-dimethyl-4-isoxazolyl)boronic acid (150 mg, 1.06 mmol), and THF (25 mL). The reaction mixture was refluxed for 24 h and cooled to RT. Standard work-up followed by column chromatography afforded 132 mg (74%) of the title product 28 as an off-white solid. $^1$H NMR (400 MHz, CDCl$_3$): δ7.26-7.21 (m, 2H), 7.17-7.14 (m, 4H), 2.41 (s, 3H), 2.28 (s, 3H), 2.0 (s, 2H), 1.95 (s, 2H), 1.31 (s, 2H), 0.96 (s, 6H), 0.93 (s, 6H). LCMS (APCI): m/z 418 (M+H)$^+$.

Example 16 (29)

3-{4-[(4-Fluorophenyl)(3,3,5,5-tetramethylcyclohexylidene)methyl]phenyl}furan (29)

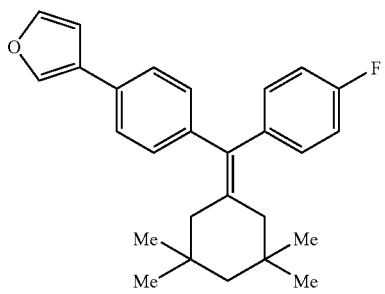

The procedure described for 28 was utilized using triflate 25 (150 mg, 0.319 mmol), PdCl$_2$ (Ph$_3$P)$_2$ (23 mg, 0.032 mmol), 2 N aqueous Na$_2$CO$_3$ (320 uL, 0.638 mmol), 3-furanylboronic acid (71 mg, 0.638 mmol), and THF (10 mL). The reaction mixture was refluxed for 15 h. Standard work-up followed by purification gave 50 mg (40%) of the title product 29 (40%) as an off-white solid. $^1$H NMR (400 MHz, CDCl$_3$): δ 7.71 (s, 1H), 7.45 (s, 1H), 7.40 (d, J=8.0 Hz, 2H), 7.18-7.12 (m, 4H), 6.96 (app. t, J=8.4 Hz, 2H), 6.68 (s, 1H), 2.0 (s, 2H), 1.96 (s, 2H), 1.30 (s, 2H), 0.94 (s, 6H), 0.93 (s, 6H). LCMS (APCI): m/z 389 (M+H)$^+$.

Example 17 (30)

2-{4-[(4-Fluorophenyl)(3,3,5,5-tetramethylcyclohexylidene)methyl]phenyl}furan (30)

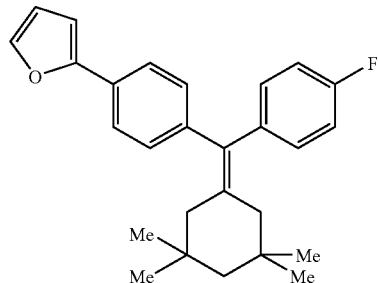

The Suzuki procedure described for 28 was utilized using triflate 25 (150 mg, 0.319 mmol), PdCl$_2$ (Ph$_3$P)$_2$ (23 mg, 0.032 mmol), 2 N aqueous Na$_2$CO$_3$ (1.6 mL, 3.2 mmol), 2-furanylboronic acid (179 mg, 1.6 mmol), and THF (2 mL). The mixture was heated at 120° C. for 15 min using microwave conditions. Standard work-up followed by purification gave 100 mg (81%) of the title product 30 as an off-white solid. $^1$H NMR (400 MHz, CDCl$_3$): δ 7.58 (d, J=8.4 Hz, 2H), 7.44 (s, 1H), 7.18-7.12 (m, 4H), 6.96 (t, J=8.8 (Hz, 2H), 6.60 (d, J=3.2 Hz, 1H), 7.45 (br s, 1H), 2.0 (s, 2H), 1.96 (s, 2H), 1.30 (s, 2H), 0.93 (s, 12H). LCMS (APCI): m/z 389 (M+H)$^+$.

Example 18 (31)

4-{4-[(4-Fluorophenyl)(3,3,5,5-tetramethylcyclohexylidene)methyl]phenyl}-1-methyl-1H-pyrazole (31)

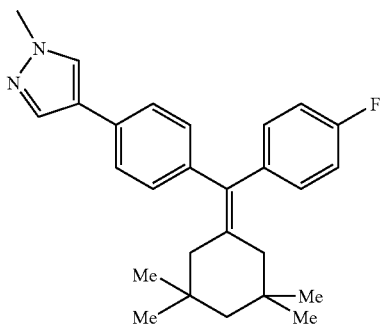

The Suzuki procedure described for 28 was followed using triflate 25 (150 mg, 0.32 mmol), PdCl$_2$(Ph$_3$P)$_2$ (23 mg, 0.032 mmol), 2 N aqueous Na$_2$CO$_3$ (320 uL, 3.2 mmol), 1-methyl-4-(4,4,5,5-tetramethyl-1,3,2-dioxaborolan-2-yl)-1H-pyrazole (334 mg, 1.6 mmol), and DME (2 mL). The mixture was heated at 120° C. for 5 min in the microwave. Aqueous work-up followed by purification gave 116 mg (90%) of the title product 31 as a white solid. $^1$H NMR (400 MHz, DMSO-d$_6$):

δ 8.06 (s, 1H), 7.79 (s, 1H), 7.46 (d, J=8.0 Hz, 2H), 7.2-7.16 (m, 2H), 7.11 (d, J=8.0 Hz, 2H), 3.83 (s, 3H), 1.93 (s, 2H), 1.88 (s, 2H), 1.26 (s, 2H), 0.89 (s, 6H), 0.84 (s, 6H). LCMS (APCI): m/z 403 (M+H)$^+$.

Example 19 (34)

({4-[Phenyl(3,3,5,5-tetramethylcyclohexylidene)methyl]phenyl}oxy)acetic acid (34)

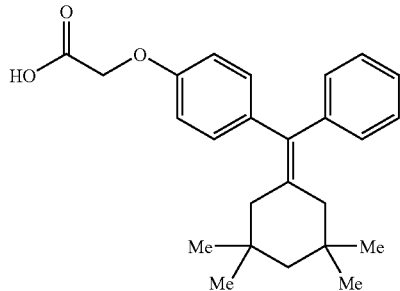

Step 1: 4-[Phenyl(3,3,5,5-tetramethylcyclohexylidene)methyl]phenol (32)

The McMurry procedure described for 9 (example 5, step 1) was utilized using (4-hydroxyphenyl)(phenyl)methanone (2.97 g, 14.9 mmol), 3,3,5,5-tetramethylcyclohexanone (6.25 g, 44.9 mmol), Zn (9.69 g, 149 mmol), TiCl$_4$.2THF complex (25 g, 7.5 mmol), and THF (200 mL). Standard work-up followed by purification gave 4.50 g (91%) of the title product 32 as a white solid. $^1$H NMR (400 MHz, CDCl$_3$): δ 7.28-7.24 (m, 2H), 7.18-7.15 (m, 3H), 7.04 (d, J=8.4 Hz, 2H), 6.74 (d, J=8.4 Hz, 2H), 1.98 (s, 2H), 1.95 (s, 2H), 1.28 (s, 2H), 0.93 (s, 6H), 0.92 (s, 6H).

Step 2: Ethyl ({4-[phenyl(3,3,5,5-tetramethylyclohexylidene)methyl]phenyl}oxy)acetate (33)

Following an O-alkylation procedure described for 10 (example 5, step 2), a round-bottomed flask was charged with compound 32 (321 mg. 1 mmol), K$_2$CO$_3$ (415 mg, 3 mmol), ethylbromoacetate (221 uL, 2 mmol), and acetone (25 mL). The reaction mixture was refluxed for 5 h, filtered, and concentrated. Purification of the crude product gave 402 mg (99%) of the title product 33. $^1$H NMR (400 MHz, CDCl$_3$): δ 7.28-7.24 (m, 2H), 7.18-7.14 (m, 3H), 7.09 (d, J=8.4 Hz, 2H), 6.81 (d, J=8.8 Hz, 2H), 4.58 (s, 2H), 4.26 (q, J=7.2 Hz, 2H), 1.97 (s, 2H), 1.95 (s, 2H), 1.28 (t, J=6.8 Hz, 3H), 0.93 (s, 6H), 0.92 (s, 6H). LCMS (ESI): m/z 405 (M−H)$^+$.

Step 3: ({4-[Phenyl(3,3,5,5-tetramethylcyclohexylidene)methyl]phenyl}oxy)acetic acid (34)

Saponification procedure described for 11 (example 5, step 3) was employed using compound 33 (310 mg, 0.76 mmol), 1N NaOH (5 mL), THF (10 mL) and EtOH (10 mL) at 70° C. for 1 h. Acidic work-up followed by purification afforded 268 mg (93%) of the title product 34 as a white solid. $^1$H NMR (400 MHz, DMSO-d$_6$): δ 7.29-7.25 (m, 2H), 7.17-7.11 (m, 2H), 7.05 (d, J=8.4 Hz, 2H), 6.80 (d, J=8.4 Hz, 2H), 1.91 (s, 2H), 1.87 (s, 2H), 1.25 (s, 2H), 0.88 (s, 6H), 0.86 (s, 6H). LCMS (ESI): m/z 377 (M−H)$^+$.

Example 20 (35)

2-({4-[Phenyl(3,3,5,5-tetramethylcyclohexylidene)methyl]phenyl}oxy)acetamide (35)

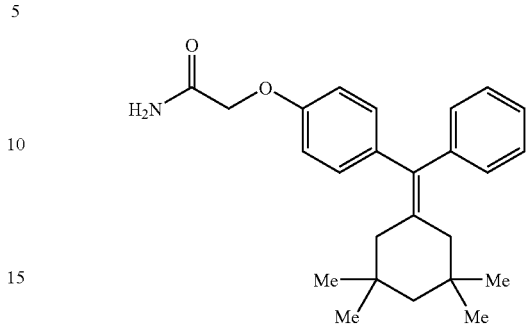

To a solution of 34 (100 mg, 0.26 mmol) and CH$_2$Cl$_2$ (mL) was added oxalyl chloride (90 uL, 1.06 mmol) and the mixture was stirred at RT for 2 h. To this solution 10 mL of NH$_4$OH (30% aqueous) was slowly introduced and stirred for 6 h. The mixture was poured into H$_2$O (100 mL) and then extracted with EtOAc (2×100 mL). The organic layer was worked-out to give the crude product, which upon purification gave 11 mg (11%) of the desired product 35 as a white solid. $^1$H NMR (400 MHz, DMSO-d$_6$): δ 7.48 (br s, 1H), 7.35 (br s, 1H), 7.27 (app. J=7.6 Hz, 2H), 7.16 (d, J=7.6 Hz, 1H), 7.12 (d, J=7.2 Hz, 2H), 7.06 (d, J=8.8 Hz, 2H), 6.85 (d, J=8.8 Hz, 2H), 4.36 (s, 2H), 1.91 (s, 2H), 1.87 (s, 2H), 1.25 (s, 2H), 0.88 (s, 6H), 0.87 (s, 6H). LCMS (ESI): m/z 378 (M+H)$^+$.

Example 21 (37)

4-({4-[Phenyl(3,3,5,5-tetramethylcyclohexylidene)methyl]phenyl}oxy)-1-butanol (37)

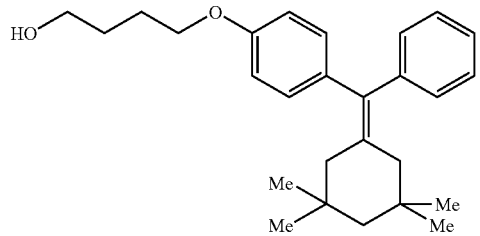

Step 1: Ethyl 4-({4-[phenyl(3,3,5,5-tetramethylcyclohexylidene)methyl]phenyl}oxy)butanoate (36)

An O-alkylation procedure described for 9 (example 5, step 2) employed using 32 (800 mg, 2.50 mmol), K$_2$CO$_3$ (1.04 g, 7.49 mmol), ethyl 4-chlorobutanoate (715 uL, 5 mmol), and acetone (30 mL). The mixture was refluxed for 15 h and cooled to RT. The mixture was filtered, concentrated, and purified to give ~1.05 g (purity 80%) of the title product 36. This material was used as such without purification.

Step 2: 4-({4-[Phenyl(3,3,5,5-tetramethylcyclohexylidene)methyl]phenyl}oxy)-1-butanol (37)

The LAH reduction procedure described for 15 (example 5) was utilized using 36 (200 mg, 0.46 mmol), LAH (1 M solution in THF, 1.4 mL, 1.38 mmol) in THF (30 mL). The reaction was stirred for 0.5 h. Standard aqueous work-up followed by purification gave 126 mg (70%) of the title product 37 as a white solid. $^1$H NMR (400 MHz, CDCl$_3$): δ 7.28-7.24 (m, 2H), 7.18-7.14 (m, 3H), 7.07 (d, J=8.4 Hz, 2H), 6.79 (d, J=8.4 Hz, 2H), 3.97 (t, J=6.0 Hz, 2H), 3.71 (br m, 2H), 1.98 (s, 2H), 1.95 (s, 2H), 1.88-1.84 (pentet, J=6.0 Hz, 2H), 1.78-1.70 (pentet, J=5.6 Hz, 2H), 1.28 (s, 2H), 0.93 (s, 6H), 0.92 (s, 6H). LCMS (APCI): m/z 393 (M+H)+.

Example 22 (38)

4-({4-[Phenyl(3,3,5,5-tetramethylcyclohexylidene)methyl]phenyl}oxy)butanoic acid (38)

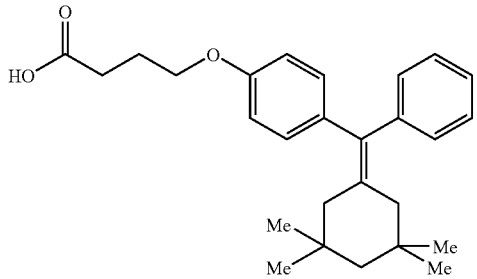

Following the saponification procedure described for 11 (example 5, step 3), compound 36 (250 mg (80% pure), 0.460 mmol) was treated with NaOH (1 N, 4 mL) in THF/EtOH (1:1, 10 mL) at 70° C. for 1 h. Acidic work-up followed by purification gave 186 mg (100%, based on the purity of starting material) of the title product 38 as a white solid. $^1$H NMR (400 MHz, DMSO-$d_6$): δ 7.27 (t, J=7.6 Hz, 2H), 7.60 (d, J=7.2 Hz, 1H), 7.12 (d, J=8.0 Hz, 2H), 7.03 (d, J=8.4 Hz, 2H), 6.82 (d, J=8.4 Hz, 2H), 3.91 (t, J=6.4 Hz, 2H), 2.34 (t, J=7.2 Hz, 2H), 1.87 (s, 2H), 1.91-1.86 (app. m, 2H), 1.24 (s, 2H), 0.88 (s, 6H), 0.86 (s, 6H). LCMS (APCI): m/z 429 (M+H)+.

Example 23 (43)

({2-Methyl-5-[phenyl(3,3,5,6-tetramethylcyclohexylidene)methyl]phenyl}oxy)acetic acid (43)

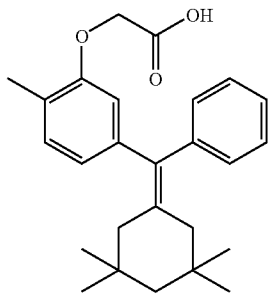

Step 1: [4-Methyl-3-(methyloxy)phenyl](phenyl)methanone (39)

N,3-dimethyl-N,4-bis(methyloxy)benzamide (Prepared from the corresponding benzoic acid following the standard literature procedure for the formation of Weinreb amide, 6.2 g, 29.6 mmol) was dissolved in anhydrous THF (110 mL) under nitrogen and the solution was cooled to 0° C. A solution of 3 M phenyl magnesium bromide in ether (15.0 mL, 44.4 mmol) was then added drop-wise while maintaining an internal temperature of 0° C. to 5° C. The resulting mixture was stirred for 3 h at 0° C. to 5° C. then quenched with 5% aqueous HCl (150 mL) and extracted with ethyl acetate (3×100 mL). The combined organic extracts were dried (MgSO$_4$), filtered, and concentrated in vacuuo to give 9.2 g of the crude 39 that was used without additional purification. $^1$H NMR (400 MHz, CDCl$_3$): δ 2.13 (s, 3H), 3.92 (s, 3H), 6.91 (d, J=8.8 Hz, 1H), 7.40-7.62 (m, 5H), 7.64-7.70 (m, 1H), 7.73-7.79 (m, 1H).

Step 2: (3-Hydroxy-4-methylphenyl)(phenyl)methanone (40)

Compound 39 (5 g, 22.1 mmol) was combined with AlCl$_3$ (9 g, 66.3 mmol) and anhydrous toluene (50 mL) in a 200 mL round bottom flask. The stirring mixture was refluxed for 1 h under nitrogen then cooled to ambient temperature and quenched with 1 N aqueous HCl (50 mL). The reaction was extracted with ethyl acetate (3×100 mL). The combined organic extracts were dried (MgSO$_4$), filtered, and the solvents removed in vacuuo. The resulting residue was treated with 10% EtOAc/hexanes at which time a solid precipitated from the solvent. The solid was filtered and dried in vacuuo for 4 h to give 3.1 g (70%) of compound 40 as an ash solid. $^1$H NMR (400 MHz, CDCl$_3$): δ 2.13 (s, 3H), 7.10-7.62 (m, 6H), 7.64-7.72 (m, 2H).

Step 3: 2-Ethyl-5-[phenyl(3,3,5,5-tetramethylcyclohexylidene)methyl]phenol (41)

To a stirred suspension of Zn powder (2.0 g, 36.0 mmol) and THF (50 mL) under N$_2$ was added TiCl$_4$ (6.0 g, 18.0 mmol). The resulting yellow suspension was refluxed for 1 h. A solution of 3,3,5,5-tetramethylcyclohexanone (1.6 g, 10.7 mmol) and compound 40 (1.00 g, 3.6 mmol) in THF (50 mL) was added dropwise to the refluxing reaction over 15 min. After 2 h, the reaction was cooled to RT and then poured into 150 mL 50% aqueous HCl and stirred for 30 min. The mixture was then diluted with EtOAc (150 mL) and the phase separated. The aqueous phase was washed with 2×100 mL EtOAc and the combined organics washed with brine (150 mL). The organics were then dried over MgSO$_4$, filtered, and the solvents removed in vacuuo. The crude material was purified by column chromatography on silica gel (150 g) with 20% EtOAc to give a the desired product contaminated with 3% of 3,3,5,5-tetramethylcyclohexanone. The desired product was recrystallized from hexanes to give 1.8 g (48%) of 41 as a colorless solid. $^1$H NMR (400 MHz, CDCl$_3$): δ 0.89 (s, 6H), 0.93 (s, 6H), 1.25 (s, 2H), 1.75 (s, 2H), 1.90 (s, 2H), 2.13 (s, 3H), 6.57-6.89 (m, 3H), 7.01-7.30 (m, 5H), 9.15 (s, 1H).

Step 4: Ethyl ({2-methyl-5-[phenyl(3,3,5,5-tetramethylcyclohexylidene)methyl]phenyl}oxy)acetate (42)

Bromoethylacetate (187 mg, 1.12 mmol), compound 41 (150 mg, 0.449 mmol), and K$_2$CO$_3$ (185 mg, 1.34 mmol) were combined with dry acetone (5 mL) in a sealed microwave vessel. The mixture was heated at 100° C. for 20 minutes in a Personal Chemistry Emrys Optimizer microwave. The reaction was allowed to cool to room temperature and the solids filtered. The solids were rinsed twice with acetone and the solvent was removed in vacuuo to give 187 mg (99%) of compound 42. The crude material was used without additional purification. $^1$H NMR (400 MHz, CDCl$_3$): δ 0.88 (s, 6H), 0.91 (s, 6H), 1.20-1.25 (m, 5H), 1.75 (s, 2H), 1.90 (s, 2H), 2.23 (s, 3H), 4.22 (m, 3H), 4.46 (s, 2H), 6.73 (d, J=8.3 Hz, 1H), 6.75-7.05 (m, 2H), 7.09-7.46 (m, 5H).

Step 5: ({2-Methyl-5-[phenyl(3,3,5,5-tetramethylcyclohexylidene)methyl]phenyl}oxy)acetic acid (43)

Compound 42 (50 mg, 0.12 mmol), NaOH (50 mg, 1.25 mmol), ethanol (5 mL) and water (500 uL) were combined in a sealed microwave vessel. The mixture was heated at 100° C. for 10 minutes in a Personal Chemistry Emrys Optimizer microwave. The reaction was then acidified with 1 N HCl (5 mL) and extracted with EtOAc (3×10 mL). The combined organic extracts were dried over MgSO$_4$, filtered, and the solvents removed in vacuuo to give 46 mg (98%) of 43 as a purple solid. $^1$H NMR (400 MHz, CDCl$_3$): δ 0.88 (s, 6H), 0.91 (s, 6H), 1.20-1.25 (m, 5H), 1.75 (s, 2H), 1.90 (s, 2H), 2.23 (s, 3H), 4.61 (s, 2H), 6.74 (d, J=8.3 Hz, 1H), 6.75-7.05 (m, 2H), 7.09-7.15 (m, 3H) 7.25-7.36 (m, 2H).

Example 24 (44)

2-({2-Methyl-5-[phenyl(3,3,5,5-tetramethylcyclohexylidene)methyl]phenyl}oxy)ethanol (44)

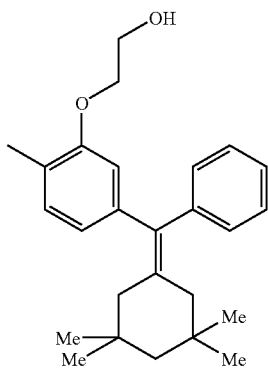

Compound 42 (93 mg, 0.22 mmol) was dissolved in THF (5 mL) and cooled to 0° C. under nitrogen. DIBAL-H (1M in hexane, 370 µL, 0.55 mmol) was added drop-wise over several minutes. The ice bath was removed and the stirring reaction allowed to warm to ambient temperature. The reaction was re-cooled to 0° C. and water (10 mL) added dropwise over several minutes. The ice bath was removed and the reaction stirred until solids began to form. The solids were filtered and the filtrate washed several time with dichloromethane to ensure all product was removed from the aluminate solids. The filtrate was concentrated in vacuuo to give 82 mg (98%) of compound 44 as a white solid. $^1$H NMR (400 MHz, CDCl$_3$): δ 0.88 (s, 6H), 0.91 (s, 6H), 1.25 (s, 2H), 1.77 (s, 2H), 1.90 (s, 2H), 2.20 (s, 3H), 3.91-3.98 (m, 2H), 4.02-4.15 (m, 2H), 6.68 (d, J=8.1 Hz, 1H) 6.75-7.05 (m, 2H), 7.09-7.15 (m, 3H) 7.25-7.36 (m, 2H).

Example 25 (45)

({2-Methyl-5-[phenyl(3,3,5,5-tetramethylcyclohexylidene)methyl]phenyl}oxy)acetonitrile (45)

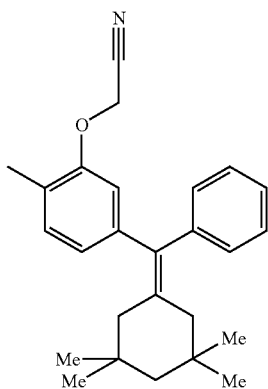

Bromoacetonitrile (134 mg, 1.12 mmol), compound 41 (150 mg, 0.449 mmol), and K$_2$CO$_3$ (185 mg, 1.34 mmol) were combined with dry acetone (5 mL) in a sealed microwave vessel. The mixture was heated at 100° C. for 20 min in a Personal Chemistry Emrys Optimizer microwave. The reaction was allowed to cool to room temperature and the solids filtered. The solids were rinsed twice with acetone and the solvent removed in vacuuo. The crude mixture was purified using flash column chromatography with dichloromethane as the eluent to give 60 mg (36%) of 45 as a colorless solid (36%). $^1$H NMR (400 MHz, CDCl$_3$): δ 0.88 (s, 6H), 0.91 (s, 6H), 1.25 (s, 2H), 1.77 (s, 2H), 1.90 (s, 2H), 2.20 (s, 3H), 4.62-4.68 (s, 2H), 6.78 (d, J=8.1 Hz, 1H) 6.75-7.05 (m, 2H), 7.09-7.25 (m, 5H).

Example 26 (47)

4-({2-Methyl-5-[phenyl(3,3,5,5-tetramethylcyclohexylidene)methyl]phenyl}oxy)butanoic acid (47)

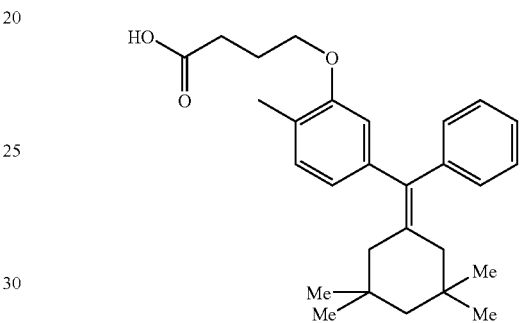

Step 1: Ethyl 3-({2-methyl-5-[phenyl(3,3,5,5-tetramethylcyclohexylidene)methyl]phenyl}oxy)propanoate (46)

Ethyl 4-bromobutanoate (219 mg, 1.12 mmol), compound 40 (150 mg, 0.449 mmol), and K$_2$CO$_3$ (185 mg, 1.34 mmol) were combined with dry acetone (5 mL) in a sealed microwave vessel. The mixture was heated at 100° C. for 20 minutes in a Personal Chemistry Emrys Optimizer microwave. The reaction was allowed to cool to room temperature and the solids filtered. The solids were rinsed twice with acetone and the solvent removed in vacuuo to give 200 mg (98%) of compound 46 and the crude material was used without additional purification. $^1$H NMR (400 MHz, CDCl$_3$): δ 0.89 (s, 6H), 0.93 (s, 6H), 1.20-1.29 (m, 7H), 1.75 (s, 2H), 1.87 (s, 2H), 1.97 (s, 2H), 2.13 (s, 3H), 2.59 (t, J=7.0 Hz, 2H), 3.92 (t, J=6.3 Hz, 2H), 4.05-4.25 (m, 2H), 6.70 (d, J=9.0 Hz, 1H), 6.91-6.99 (m, 2H), 7.10-7.20 (m, 3H), 7.20-7.30 (m, 2H).

Step 2: 4-({2-Methyl-5-[phenyl(3,3,5,5-tetramethylcyclohexylidene)methyl]phenyl}oxy)butanoic acid (7)

Compound 46 (53 mg, 0.12 mmol), NaOH (50 mg, 1.25 mmol), ethanol (5 mL) and water (500 uL) were combined in a sealed microwave vessel. The mixture was heated at 100° C. for 10 minutes in a Personal Chemistry Emrys Optimizer microwave. The reaction was then acidified with 1 N HCl (5 mL) and extracted with EtOAc (3×10 mL). The combined organic extracts were dried over MgSO$_4$. The solids were filtered and the solvent removed in vacuuo to give 43 mg (86%) of compound 47 as a solid. $^1$H NMR (400 MHz, CDCl$_3$): δ 0.89 (s, 6H), 0.93 (s, 6H), 1.20-1.29 (m, 4H), 1.90

(s, 2H), 1.97 (s, 2H), 2.13 (s, 3H), 2.60 (t, J=6.8 Hz, 2H), 3.72 (t, J=6.3 Hz, 2H), 3.97 (t, J=6.1 Hz, 2H), 6.70 (d, J=9.0 Hz, 1H), 6.91-6.99 (m, 2H), 7.10-7.20 (m, 3H), 7.20-7.30 (m, 2H).

Example 27 (48)

4-({2-Methyl-5-[phenyl(3,3,5,5-tetramethylcyclohexylidene)methyl]phenyl}oxy)-1-butanol (48)

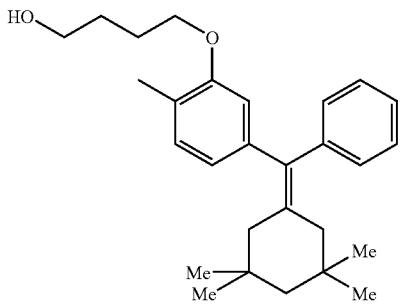

Compound 47 (50 mg, 0.11 mmol) was dissolved in THF (5 mL) and cooled to 0° C. under nitrogen. DIBAL (1.5 M in hexane, 500 ul, 0.33 mmol) was added drop-wise over several minutes. The ice bath was removed and the stirring reaction allowed to warm to ambient temperature. The reaction was then cooled back to 0° C. and water (10 mL) added dropwise over several minutes. The ice bath was then removed and the reaction was stirred until solids began to form. The solids were filtered and the filtrate washed several times with dichloromethane. The filtrate was concentrated in vacuuo to give 42 mg (98%) of compound 48 as a clear oil. $^1$H NMR (400 MHz, CDCl$_3$): δ 0.93 (s, 6H), 0.95 (s, 6H), 1.29 (s, 2H), 1.75 (s, 2H), 1.90 (s, 2H), 2.08-2.17 (m, 5H), 2.55 (t, J=7.3 Hz, 2H), 3.72 (t, J=6.3 Hz, 2H), 3.97 (t, J=6.1 Hz, 2H), 6.70 (d, J=9.0 Hz, 1H), 6.91-6.99 (m, 2H), 7.10-7.20 (m, 3H), 7.20-7.30 (m, 2H).

Example 28 (49)

5-[({2-Methyl-5-[phenyl(3,3,5,5-tetramethylcyclohexylidene)methyl]phenyl}oxy)methyl]-1H-tetrazole (49)

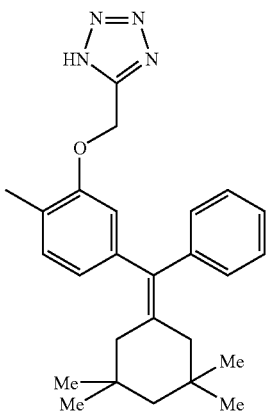

Compound 45 (50 mg, 0.13 mmol), NaN$_3$ (60 mg, 0.86 mmol), and NH$_4$Cl (50 mg, 0.94 mmol) were combined with DMF (5 mL) in a sealed microwave vessel. The mixture was heated at 100° C. for 20 minutes in a Personal Chemistry Emrys Optimizer microwave. The mixture was then stirred for an additional 16 h at 100° C. in an oil bath. The reaction was allowed to cool to room temperature and diluted with 5 mL of 1 N HCl. A white solid formed upon addition of HCl. EtOAc was then added to dissolve the solid and the crude reaction was extracted three times with EtOAc (10 mL each. The combined organic extracts were dried over MgSO$_4$. The solids were removed via filtration and the solvent was removed in vacuuo to give 51 mg (98%) of the desired compound 49 as a pink solid. $^1$H NMR (400 MHz, CDCl$_3$): δ 0.86 (s, 6H), 0.96 (s, 6H), 1.25 (s, 2H), 1.85-1.98 (m, 4H), 2.13 (s, 3H), 5.39 (s, 2H), 6.72 (d, J=8.8 Hz, 2H), 6.91 (d, J=8.6 Hz, 2H), 7.07-7.19 (m, 3H), 7.20-7.28 (m, 2H). LCMS (ESI): m/z 417 (M+H)$^+$.

Example 29 (50)

2-{[2-({2-Methyl-5-[phenyl(3,3,5,5-tetramethylcyclohexylidene)methyl]phenyl}oxy)ethyl]oxy}ethanol (50)

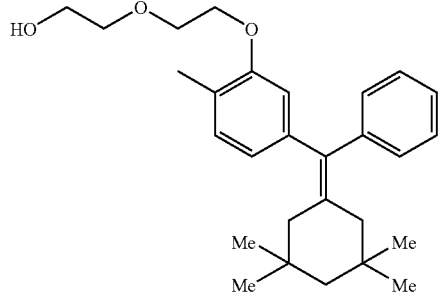

2-(2-chloroethoxy)ethanol (139 mg, 1.12 mmol), compound 41 (150 mg, 0.45 mmol), and K$_2$CO$_3$ (185 mg, 1.34 mmol) were combined with dry acetone (5 mL) in a sealed microwave vessel. The mixture was heated at 100° C. for 20 minutes in a Personal Chemistry Emrys Optimizer microwave. The reaction was allowed to cool to room temperature and the solids were removed via filtration. The solids were rinsed twice with acetone and the solvent was removed in vacuuo. The reaction was purified using the Agilent semi prep HPLC (LUNA C18 column, 23 mL/min, 30-70% CH$_3$CN-Water (TFA) to give 76 mg (40%) of the desired compound 50 as a white solid. $^1$H NMR (400 MHz, CDCl$_3$): δ 0.91 (s, 6H), 0.93 (s, 6H), 1.23 (s, 2H), 1.95 (s, 2H), 1.96 (s, 2H), 2.13 (s, 3H), 3.7-3.78 (m, 2H), 3.87 (t, J=4.6 Hz, 2H), 4.1 (t, J=4.8 Hz, 2H), 6.72 (d, J=8.8 Hz, 2H), 7.13 (d, J=8.6 Hz, 2H), 7.10-7.20 (m, 3H), 7.20-7.30 (m, 2H).

Prophetic Examples

The following compounds can be prepared analogously using the descriptions of synthesis herein provided. Although slight variations in synthetic procedure may be necessary, all should be within the ordinary skill of the art.

Prophetic Example 30

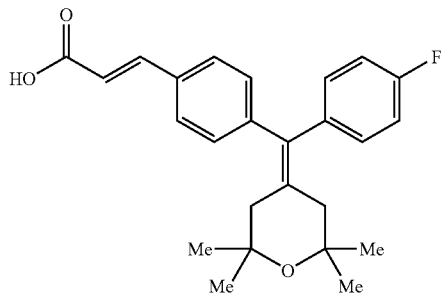

(2E)-3-{4-[(4-Fluorophenyl)(2,2,6,6-tetramethyltetrahydro-4H-pyran-4-ylidene)methyl]phenyl}-2-propenoic acid (51)

Prophetic Example 31

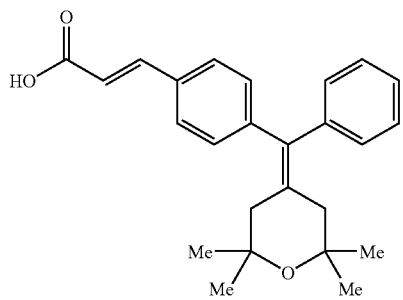

(2E)-3-{4-[Phenyl(2,2,6,6-tetramethyltetrahydro-4H-pyran-4-ylidene)methyl]phenyl}-2-propenoic acid (52)

Prophetic Example 32

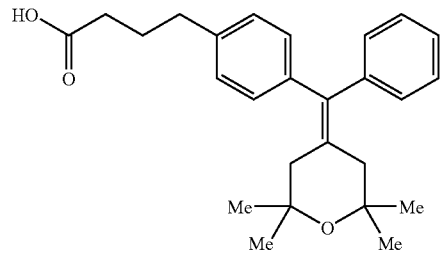

4-{4-[Phenyl(2,2,6,6-tetramethyltetrahydro-4H-pyran-4-ylidene)methyl]phenyl}butanoic acid (53)

Prophetic Example 33

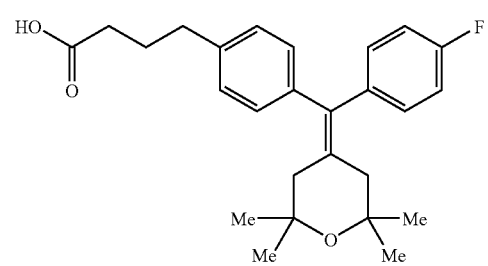

4-{4-[(4-Fluorophenyl)(2,2,6,6-tetramethyltetrahydro-4H-pyran-4-ylidene)methyl]phenyl}butanoic acid (54)

Prophetic Example 34

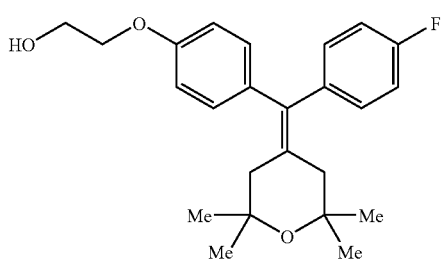

2-({4-[(4-Fluorophenyl)(2,2,6,6-tetramethyltetrahydro-4H-pyran-4-ylidene)methyl]phenyl}oxy)ethanol (55)

Prophetic Example 35

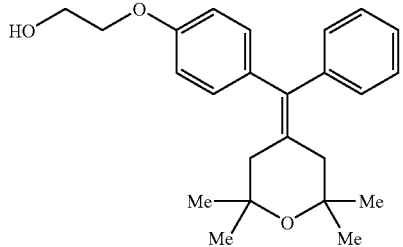

2-({4-[Phenyl(2,2,6,6-tetramethyltetrahydro-4H-pyran-4-ylidene)methyl]phenyl}oxy)ethanol (56)

Prophetic Example 36

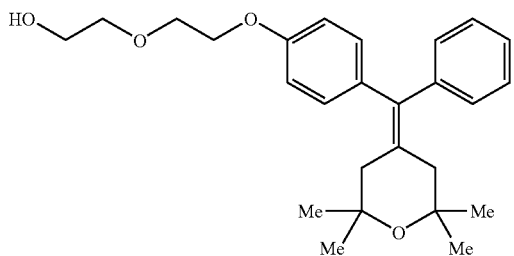

2-{[2-({4-[Phenyl(2,2,6,6-tetramethyltetrahydro-4H-pyran-4-ylidene)methyl]phenyl}oxy)ethyl]oxy}ethanol (57)

Prophetic Example 37

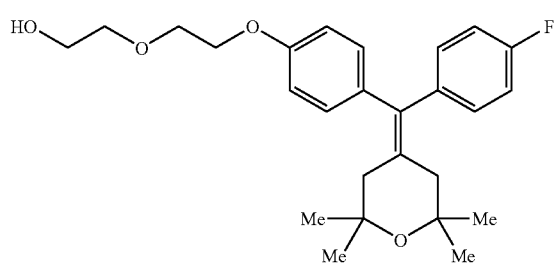

2-{[2-({4-[(4-Fluorophenyl)(2,2,6,6-tetramethyltetrahydro-4H-pyran-4-ylidene)methyl]phenyl}oxy)ethyl]oxy}ethanol (58)

Prophetic Example 38

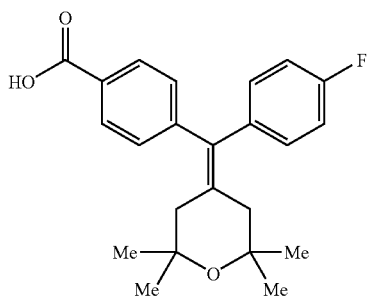

4-[(4-Fluorophenyl)(2,2,6,6-tetramethyltetrahydro-4H-pyran-4-ylidene)methyl]benzoic acid (59)

Prophetic Example 39

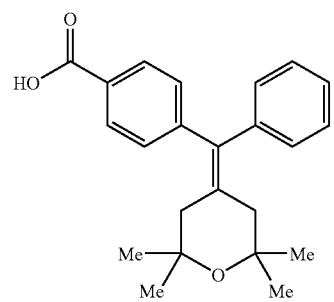

4-[Phenyl(2,2,6,6-tetramethyltetrahydro-4H-pyran-4-ylidene)methyl]benzoic acid (60)

Prophetic Example 40

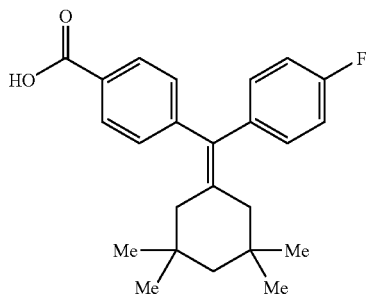

4-[(4-Fluorophenyl)(3,3,5,5-tetramethylcyclohexylidene)methyl]benzoic acid (61)

Biological Data

ER Alpha Fluorescence Polarisation Assays.

Assays were conducted on the non-prophetic exemplary compounds (shown above in the Examples) using both full length and ligand binding domain protein.

Full length ER alpha—The assay was performed using a commercially available kit (P3029, Invitrogen, Carlsbad, Calif.). The assay was performed according to the manufacturer's protocol with minor amendments. Namely, 15 nM ERα and 1 nM Fluormone EL Red were dissolved and mixed in Complete ER Red Buffer. 10 μl of the mix was dispensed to each well of Greiner low volume plates—Black solid low volume 384-well plates—(Greiner—Product No. 784076), containing compounds within the concentration range of $10^{-5}$-$10^{-12}$M in dimethyl sulfoxide (DMSO). The plates were spun for 1 min at 200 g, covered to protect the reagents from light, and then incubated at room temperature for 2 hours. Plates were read on an Acquest, LJL Biosystems, Sunnyvale, Calif., using a 530-25 nm excitation and 580-10 nm emission interference filter and a 561 nm Dichroic mirror.

```
ER alpha (ligand binding domain)-
Sequence of 6x His ERα LBD (297-555)
MKKGHHHHHHGLVPRGSMIKRSKKNSLALSLTADQMVSALLDAEPPILYS

EYDPTRPFSEASMMGLLTNLADRELVHMINWAKRVPGFVDLTLHDQVHLL

ECAWLEILMIGLVWRSMEHPGKLLFAPNLLLDRNQGKCVEGMVEIFDMLL

ATSSRFRMMNLQGEEFVCLKSIILLNSGVYTFLSSTLKSLEEKDHIHRVL

DKITDTLIHLMAKAGLTLQQQHQRLAQLLLILSHIRHMSNKGMEHLYSMK

CKNVVPLYDLLLEMLDAHRLHAPTS
```

Expression and Purification of ERα LBD

A cDNA sequence corresponding to residues 297 to 555 of human ERα was cloned into a pET24vector (Novagen, San Diego, Calif.) with a N-terminal hexa-histidine tag. The plasmid was transformed into *E. Coli* BL21-DE3 cells. Cells were grown at 23° C. for 18 hr, the temperature was lowered to 18° C. before addition of 250 μM IPTG. Cells were grown an additional 24 hr before harvesting. Cells were lysed in 50 mM TRIS pH 8.0/250 mM NaCl/2 M Urea and spun down. The supernatant was made 50 mM in imidazole and loaded onto a Ni-chelating sepharose column (Pharmicia) and eluted with a linear gradient of 50 to 500 mM Imidazole. Fractions containing ERα LBD were pooled and dialyzed against 50 mM TRIS pH 8.0/250 mM NaCl/5 mM DTT and 10% glycerol. Samples were aliquoted and frozen at −70° C. The assay was performed by mixing 15 nM ER alpha LBD with 1 nM Fluormone-EL-Red (Invitrogen No. P3030) in assay buffer (Tris-HCl (50 mM; pH8), KCl, (500 mM), Dithiothreitol (1 mM), Ethylene diamine tetraacetic acid (1 mM), glycerol (10% v/v), 3 cholamidopropyl-dimethylammonio 1—propanesulfonate—(2 mM), Sodium orthovanadate (1 mM—this was prepared as 100 mM stock by dissolving in distilled water and 2 successive rounds of adjusting pH to 10, boiling and cooling)). 10 μl of the mix was dispensed to each well of Greiner low volume plates—Black solid low volume 384-well plates—(Greiner, Longwood, Fla. —Product No. 784076), containing compounds within the concentration range of $10^{-5}$-$10^{-12}$M in dimethyl sulfoxide (DMSO). The plates were spun for 1 min at 200 g, covered to protect the reagents from light, and then incubated at room temperature for 2 hours. Plates were read on the Acquest using a 530-25 nm excitation and 580-10 nm emission interference filter and a 561 nm Dichroic mirror.

ER Beta Fluorescence Polarisation Assays.

Assays were conducted using both full length and ligand binding domain protein. Full length ER beta—The assay was performed using a commercially available kit (P3032, Invitrogen). The assay was performed according to the manufacturer's protocol with minor amendments. Namely, 30 nM ERβ and 1 nM Fluormone EL Red were dissolved and mixed in Complete ER Red Buffer. 10 μl of the mix was dispensed to each well of Greiner low volume plates—Black solid low volume 384-well plates—(784076, Greiner), containing compounds within the concentration range of $10^{-5}$-$10^{-12}$M in dimethyl sulfoxide (DMSO). The plates were spun for 1 min at 200 g, covered to protect the reagents from light, and then incubated at room temperature for 2 hours. Plates were read on an Acquest (Acquest/Biosystems) using a 530-25 nm excitation and 580-10 nm emission interference filter and a 561 nm Dichroic mirror.

```
ER beta (ligand binding domain)-
Sequence of 6x His ERβ LBD (257-530)
MKKHHHHHHG ELLLDALSPE QLVLTLLEAE PPHVLISRPS

APFTEASMMM SLTKLADKEL VHMISWAKKI PGFVELSLFD

QVRLLESCWM EVLMMGLMWR SIDHPGKLIF APDLVLDRDE

GKCVEGILEI FDMLLATTSR FRELKLQHKE YLCVKAMILL

NSSMYPLVTA TQDADSSRKL AHLLNAVTDA LVWVIAKSGI

SSQQQSMRLA NLLMLLSHVR HASNKGMEHL LNMKCKNVVP

VYDLLLEMLN AHVLRGCKSS ITGSECSPAE DSKSKEGSQN

PQSQ
```

Expression and Purification of ERβ LBD

A cDNA sequence corresponding to residues 257 to 530 of human ERβ was cloned into a pRSETa (Novagen) vector with a N-terminal hexa-histidine tag. The plasmid was transformed into *E. Coli* BL21-DE3 cells. The cells were grown at 23° C. for 18 hr, the temperature was lowered to 18° C. and then 250 μM of IPTG was added. Cells were grown an additional 24 hr before harvesting. Cells were lysed in 50 mM TRIS pH 8.0/250 mM NaCl and spun down. The supernatant was made 50 mM in imidazole and loaded onto a Ni-chelating sepharose column (Amersham Pharmacia Biotech, Piscataway, N.J.) and eluted with a linear gradient of 50 to 500 mM Imidazole. Fractions containing ERβ LBD were pooled and diluted to 50 mM NaCl and loaded on a Q-sepharose column (Pharmacia) equilibrated with 50 mM TRIS pH 8.0/50 mM NaCl/5 mM DTT and 10% glycerol. The ERβ was eluted with a linear gradient from 50 mM to 500 mM NaCl. Fractions containing ERβ LBD were pooled and dialyzed against 50 mM TRIS pH 8.0/250 mM NaCl/5 mM DTT and 10% glycerol. Samples were aliquoted and frozen at −70° C.

The assay was performed by mixing 30 nM ER beta LBD with 1 nM Fluormone-EL-Red (Invitrogen No. P3030) in assay buffer (Tris-HCl (50 mM; pH8), KCl, (500 mM), Dithiothreitol (1 mM), Ethylene diamine tetraacetic acid (1 mM), glycerol (10% v/v), 3 cholamidopropyl-dimethylammonio1—propanesulfonate—(2 mM), Sodium orthovanadate (1 mM—this was prepared as 100 mM stock by dissolving in distilled water and 2 successive rounds of adjusting pH to 10, boiling and cooling)). 10 μl of the mix was dispensed to each well of black solid low volume 384-well plates—(784076, Greiner), containing compounds within the concentration range of $10^{-5}$-$10^{-12}$M in dimethyl sulfoxide (DMSO). The plates were spun for 1 min at 200 g, covered to protect the reagents from light, and then incubated at room temperature for 2 hours. Plates were read on the Acquest using a 530-25 nm excitation and 580-10 nm emission interference filter and a 561 nm Dichroic mirror.

Data Analysis

All data was normalized to the mean of 16 high and 16 low control wells on each plate. A four parameter curve fit of the following form was then applied $$y = \frac{a-d}{1+(x/c)^b} + d$$

Where a is the minimum, b is the Hill slope, c is the $IC_{50}$ and d is the maximum. Data is presented as the mean $pIC_{50}$ with the standard deviation of the mean of n experiments.

The compounds of the non-prophetic Examples above exhibited pIC$_{50}$ values ranging from 6 to 8.5.

Test compounds were employed in free or salt form.

All research complied with the principles of laboratory animal care (NIH publication No. 85-23, revised 1985) and GlaxoSmithKline policy on animal use.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A compound of formula (I-A):

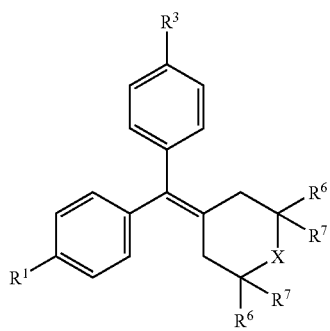

(I-A)

including pharmaceutically acceptable salts thereof wherein
$R^1$ is H or F;
$R^3$ is —(Y)$_z$—$R^8$;
z is 0 or 1;
Y is —CH=CH—;
each of $R^6$ and $R^7$ are selected from H or alkyl;
when z is 0, then $R^8$ is —O(CH$_2$)$_t$CN, —CO$_2$H, —(CH$_2$)$_t$CO$_2$H, —O(CH$_2$)$_t$CO$_2$H, —O(CH$_2$)$_t$OH, —O(CH$_2$)$_t$O(CH$_2$)$_t$OH, or —O(CH$_2$)$_t$C(O)NH$_2$;
when z is 1, then $R^8$ is —CO$_2$H or —CONH$_2$;
each t independently is 1 to 8; and
X is —(CH$_2$)$_n$—, where n is 0, 1, or 2, or O.

2. A compound selected from:
(2E)-3-{4-[Cycloheptylidene(phenyl)methyl]phenyl}prop-2-enoic acid;
(2E)-3-{4-[Cycloheptylidene(phenyl)methyl]phenyl}prop-2-enamide;
2-({4-[Phenyl(3,3,5,5-tetramethylcyclohexylidene)methyl]phenyl}oxy)ethanol;
2-{[2-({4-[Phenyl (3,3,5,5-tetramethylcyclohexylidene)methyl]phenyl}oxy)ethyl]oxy}ethanol;
({4-[(4-Fluorophenyl)(3,3,5,5-tetramethylcyclohexylidene)methyl]phenyl}oxy)acetic acid;
4-({4-[(4-Fluorophenyl)(3,3,5,5-tetramethylcyclohexylidene)methyl]phenyl}oxy)butanoic acid;
({4-[(4-Fluorophenyl)(3,3,5,5-tetramethylcyclohexylidene)methyl]phenyl}oxy)acetonitrile;
2-({4-[(4-Fluorophenyl)(3,3,5,5-tetramethylcyclohexylidene)methyl]phenyl}oxy)ethanol;
(2E)-3-{4-[Phenyl(3,3,5,5-tetramethylcyclohexylidene)methyl]phenyl}-2-propenoic acid;
4-[Phenyl(3,3,5,5-tetramethylcyclohexylidene)methyl]benzoic acid;
2-{[2-({4-[(4-Fluorophenyl)(3,3,5,5-tetramethylcyclohexylidene)methyl]phenyl}oxy)ethyl]oxy}ethanol;
4-({4-[Phenyl(3,3,5,5-tetramethylcyclohexylidene)methyl]phenyl}oxy)-1-butanol;
2-({4-[Phenyl(3,3,5,5-tetramethylcyclohexylidene)methyl]phenyl}oxy)acetamide;
4-({4-[Phenyl(3,3,5,5-tetramethylcyclohexylidene)methyl]phenyl}oxy)butanoic acid;
({4-[Phenyl(3,3,5,5-tetramethylcyclohexylidene)methyl]phenyl}oxy)acetic acid;
(2E)-3-{4-[(4-Fluorophenyl)(3,3,5,5-tetramethylcyclohexylidene)methyl]phenyl}-2-propenoic acid;
(2E)-3-{4-[(4-Fluorophenyl)(2,2,6,6-tetramethyltetrahydro-4H-pyran-4-ylidene)methyl]phenyl}-2-propenoic acid;
(2E)-3-{4-[Phenyl (2,2,6,6-tetramethyltetrahydro-4H-pyran-4-ylidene)methyl]phenyl}-2-propenoic acid;
4-{4-[Phenyl (2,2,6,6-tetramethyltetrahydro-4H-pyran-4-ylidene)methyl]phenyl}butanoic acid;
4-{4-[(4-Fluorophenyl)(2,2,6,6-tetramethyltetrahydro-4H-pyran-4-ylidene)methyl]phenyl}butanoic acid;
2-({4-[(4-Fluorophenyl)(2,2,6,6-tetramethyltetrahydro-4H-pyran-4-ylidene)methyl]phenyl}oxy)ethanol;
2-({4-[Phenyl(2,2,6,6-tetramethyltetrahydro-4H-pyran-4-ylidene)methyl]phenyl}oxy)ethanol;
2-{[2-({4-[Phenyl(2,2,6,6-tetramethyltetrahydro-4H-pyran-4-ylidene)methyl]phenyl}oxy)ethyl]oxy}ethanol;
2-{[2-({4-[(4-Fluorophenyl)(2,2,6,6-tetramethyltetrahydro-4H-pyran-4-ylidene)methyl]phenyl}oxy)ethyl]oxy}ethanol;
4-[(4-Fluorophenyl)(2,2,6,6-tetramethyltetrahydro-4H-pyran-4-ylidene)methyl]benzoic acid;
4-[Phenyl(2,2,6,6-tetramethyltetrahydro-4H-pyran-4-ylidene)methyl]benzoic acid; and
4-[(4-Fluorophenyl)(3,3,5,5-tetramethylcyclohexylidene)methyl]benzoic acid, including pharmaceutically acceptable salts thereof.

3. The compound of claim 1:

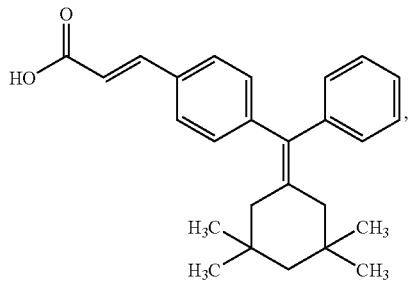

including pharmaceutically acceptable salts thereof.

4. The compound of claim 1:

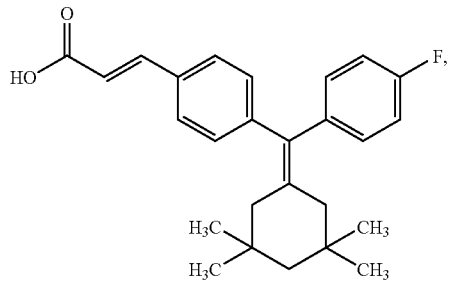

including pharmaceutically acceptable salts thereof.

5. A pharmaceutical composition comprising a compound according to claim 1, and a pharmaceutically acceptable carrier.

6. A compound according to claim 1 wherein said compound is an active therapeutic substance.

7. A compound according to claim 1 wherein said compound is an modulator.

* * * * *